United States Patent
Pepin et al.

(10) Patent No.: US 12,048,846 B2
(45) Date of Patent: Jul. 30, 2024

(54) NEUROMODULATION THERAPY SIMULATOR

(71) Applicant: Rune Labs, Inc., San Francisco, CA (US)

(72) Inventors: Brian Marc Pepin, San Francisco, CA (US); Miroslav Tchavdarov Kotzev, Pacifica, CA (US)

(73) Assignee: Rune Labs, Inc., San Francisco, CA (US)

( * ) Notice: Subject to any disclaimer, the term of this patent is extended or adjusted under 35 U.S.C. 154(b) by 946 days.

(21) Appl. No.: 16/997,762

(22) Filed: Aug. 19, 2020

(65) Prior Publication Data

US 2021/0052900 A1    Feb. 25, 2021

Related U.S. Application Data

(60) Provisional application No. 62/889,201, filed on Aug. 20, 2019.

(51) Int. Cl.
*A61N 1/36* (2006.01)
*A61N 1/05* (2006.01)
(Continued)

(52) U.S. Cl.
CPC ....... *A61N 1/36128* (2013.01); *A61N 1/0531* (2013.01); *G16H 10/60* (2018.01); *G16H 20/40* (2018.01); *G16H 40/63* (2018.01)

(58) Field of Classification Search
CPC .............. A61N 1/36128; A61N 1/0531; A61N 1/37264; G16H 10/60; G16H 20/40; G16H 40/63; G16H 40/67; G16H 20/30
See application file for complete search history.

(56) References Cited

U.S. PATENT DOCUMENTS 8,388,555 B2   3/2013  Panken et al.
9,215,075 B1   12/2015 Poltorak
(Continued)

FOREIGN PATENT DOCUMENTS

EP    0689316 A2   12/1995
EP    1439661 A1    7/2004
(Continued)

OTHER PUBLICATIONS

PCT/US2020/047141 , "International Preliminary Report on Patentability", Mar. 3, 2022, 7 pages.
(Continued)

*Primary Examiner* — Shon G Foley
(74) *Attorney, Agent, or Firm* — Mughal Gaudry & Franklin PC

(57) ABSTRACT

Methods and systems are provided for simulating neuromodulation therapy. An identification of a particular neuromodulation-therapy implant device, an identification of a particular neuromodulation-therapy algorithm, and subject records corresponding to a subject may be received. neuromodulation-therapy simulator may execute to generated predicted performance metric for the particular neuromodulation-therapy implant device. The predicted performance may correspond to predicted physiological responses of the subject when the particular neuromodulation-therapy algorithm is executed by the particular neuromodulation-therapy implant device. The predicted performance metrics may be output.

20 Claims, 23 Drawing Sheets

(51) Int. Cl.
*G16H 10/60* (2018.01)
*G16H 20/40* (2018.01)
*G16H 40/63* (2018.01)

(56) References Cited

U.S. PATENT DOCUMENTS

| | | | |
|---|---|---|---|
| 9,460,384 | B2 | 10/2016 | Levin et al. |
| 10,320,569 | B1 | 6/2019 | Wentz et al. |
| 2004/0073276 | A1 | 4/2004 | Samuelsson |
| 2004/0260363 | A1 | 12/2004 | Arx et al. |
| 2005/0204134 | A1 | 9/2005 | Arx et al. |
| 2006/0049957 | A1 | 3/2006 | Surgenor et al. |
| 2007/0167991 | A1 | 7/2007 | Dilorenzo |
| 2009/0058635 | A1 | 3/2009 | LaLonde et al. |
| 2009/0063193 | A1 | 3/2009 | Barton et al. |
| 2009/0125084 | A1 | 5/2009 | Juels et al. |
| 2011/0029038 | A1 | 2/2011 | Hyde et al. |
| 2011/0160796 | A1 | 6/2011 | Lane et al. |
| 2011/0172927 | A1 | 7/2011 | Sahasrabudhe et al. |
| 2012/0078648 | A1 | 3/2012 | Reiner |
| 2012/0204032 | A1 | 8/2012 | Wilkins et al. |
| 2013/0154851 | A1 | 6/2013 | Gaskill et al. |
| 2014/0058292 | A1 | 2/2014 | Alford et al. |
| 2014/0257047 | A1 | 9/2014 | Sillay et al. |
| 2014/0273824 | A1 | 9/2014 | Fenner et al. |
| 2015/0012057 | A1 | 1/2015 | Carlson et al. |
| 2015/0246231 | A1 | 9/2015 | Martens et al. |
| 2015/0341785 | A1 | 11/2015 | Young et al. |
| 2015/0356250 | A1 | 12/2015 | Polimeni |
| 2015/0363562 | A1 | 12/2015 | Hallwachs |
| 2015/0381659 | A1 | 12/2015 | Khazan et al. |
| 2016/0001096 | A1 | 1/2016 | Mishelevich |
| 2016/0008632 | A1 | 1/2016 | Wetmore et al. |
| 2016/0029960 | A1 | 2/2016 | Toth et al. |
| 2016/0121109 | A1 | 5/2016 | Edgerton et al. |
| 2016/0235352 | A1 | 8/2016 | Dilorenzo |
| 2016/0250472 | A1 | 9/2016 | Carbunaru |
| 2016/0317077 | A1 | 11/2016 | Sillay |
| 2017/0043167 | A1 | 2/2017 | Widge et al. |
| 2017/0095667 | A1 | 4/2017 | Yakovlev et al. |
| 2017/0098041 | A1 | 4/2017 | Paffel et al. |
| 2017/0113046 | A1 | 4/2017 | Fried et al. |
| 2017/0118019 | A1 | 4/2017 | Yang et al. |
| 2017/0180419 | A1 | 6/2017 | Pedersen et al. |
| 2017/0208464 | A1 | 7/2017 | Guertler et al. |
| 2017/0246481 | A1* | 8/2017 | Mishelevich .......... A61N 2/006 |
| 2017/0259072 | A1 | 9/2017 | Newham et al. |
| 2017/0295180 | A1 | 10/2017 | Day et al. |
| 2017/0348049 | A1 | 12/2017 | Vrba et al. |
| 2018/0133504 | A1 | 5/2018 | Malchano et al. |
| 2018/0243573 | A1 | 8/2018 | Yoder et al. |
| 2018/0333587 | A1 | 11/2018 | Howard |
| 2019/0014147 | A1 | 1/2019 | Pedersen et al. |
| 2019/0036886 | A1 | 1/2019 | Wu et al. |
| 2019/0184171 | A1 | 6/2019 | Mustakos et al. |
| 2019/0247650 | A1 | 8/2019 | Tran |
| 2020/0086128 | A1 | 3/2020 | Rondoni et al. |
| 2020/0127828 | A1 | 4/2020 | Liu et al. |
| 2020/0246621 | A1* | 8/2020 | Hofius .................. G16H 40/67 |
| 2020/0305716 | A1 | 10/2020 | Mondello et al. |
| 2021/0057089 | A1 | 2/2021 | Pepin et al. |
| 2021/0085988 | A1 | 3/2021 | Nin et al. |

FOREIGN PATENT DOCUMENTS

| | | |
|---|---|---|
| EP | 3032858 A1 | 6/2016 |
| FR | 2858497 A1 | 2/2005 |
| KR | 20140045125 A | 4/2014 |
| KR | 20170124376 A | 11/2017 |
| WO | 2014025772 A2 | 2/2014 |
| WO | 2017117421 A1 | 7/2017 |
| WO | 2017190049 A1 | 11/2017 |
| WO | 2018129280 A1 | 7/2018 |
| WO | 2018156782 A1 | 8/2018 |

OTHER PUBLICATIONS

PCT/US2020/047141, "International Search Report and Written Opinion", Nov. 19, 2020, 9 pages.
PCT/US2020/047164, "International Preliminary Report on Patentability", Mar. 3, 2022, 8 pages.
PCT/US2020/047164, "International Search Report and Written Opinion", Jan. 19, 2021, 10 pages.
PCT/US2020/047176, "International Preliminary Report on Patentability", Mar. 3, 2022, 7 pages.
PCT/US2020/047176, "International Search Report and Written Opinion", Nov. 10, 2020, 9 pages.
PCT/US2020/047241, "International Preliminary Report on Patentability", Mar. 3, 2022, 7 pages.
PCT/US2020/047241, "International Search Report and Written Opinion", Nov. 10, 2020, 9 pages.
PCT/US2020/047241, "International Search Report and Written Opinion", Oct. 6, 2020, 9 pages.
PCT/US2020/047126, "International Preliminary Report on Patentability", Mar. 3, 2022, 6 pages.
PCT/US2020/047126, "International Search Report and Written Opinion", Nov. 9, 2020, 8 pages.
Pycroft et al., "Brainjacking: Implant Security Issues in Invasive Neuromodulation", World Neurosurgery, vol. 92, May 2, 2016, 33 pages.
Stanslaski et al., "Design and Validation of a Fully Implantable, Chronic, Closed-Loop Neuromodulation Device With Concurrent Sensing and Stimulation", Available Online at: https://ieeexplore.ieee.org/stamp/stamp.jsp?tp=&arnumber=6135801, IEEE Transactions on Neural Systems and Rehabilitation Engineering, vol. 20, No. 4, Jul. 2012, pp. 410-421.
U.S. Appl. No. 16/997,744, "Non-Final Office Action", Jun. 15, 2022, 10 pages.
Wenger et al., "Spatiotemporal Neuromodulation Therapies Engaging Muscle Synergies 1-3 Improve Motor Control After Spinal Cord Injury", Nat Med., vol. 22, No. 2, Available online at https://www.ncbi.nlm.nih.gov/pmc/articles/PMC5061079/pdf/emss-66334.pdf, Oct. 12, 2016, 33 pages.
Wilikens et al., "A Context-Related Authorization and Access Control Method Based on RBAC: A Case Study From the Health Care Domain", 2002, pp. 117-124.
European Search Report for European Patent Application No. 20855796.7, dated Aug. 7, 2023.
Extended European Search Report notified Aug. 17, 2023 for Patent Application No. 208555102.
Extended European Search Report notified Aug. 21, 2023 for Patent Application No. 208550806.
Extended European Search Report notified Jul. 19, 2023 for Patent Application No. 20855507.8.

* cited by examiner

NEUROMODULATION THERAPY SIMULATOR

CROSS-REFERENCE TO RELATED APPLICATIONS

This application is a non-provisional of and claims the benefit and priority under 35 U.S.C. 119(e) of U.S. Provisional Application No. 62/889,201, filed Aug. 20, 2019, entitled "Neuromodulation Therapy Simulator", which is incorporated herein by reference in its entirety for all purposes.

BACKGROUND

Neuromodulation therapy refers to various techniques of delivering electrical stimulation and/or chemical substances to specific target areas within the brain or nervous system of a subject. Such treatments may be used to treat illnesses, restore functionality to the subject, and/or relieve pain. Thus, a neuromodulation therapy applied to a subject may be defined by the particular anatomical site(s) within the subject which are stimulated, the particular hardware used to deliver stimulation to the site(s) on the subject, and stimulation parameters and properties used to define a particular type of stimulation to be delivered via the hardware. Additionally, certain neuromodulation therapy systems may be capable of sensing brain signals and other physical responses of the subject. For example, a neuromodulation therapy implant device configured to provide stimulation to the subject's brain or nervous system, also may be configured to sense brain signals which may be stored and used for subject diagnoses and to evaluate the neuromodulation therapy treatments used on the subject.

Within conventional neuromodulation therapy systems, a single computing device (e.g., the neuromodulation therapy implant), may be responsible for delivering and monitoring the subject's neuromodulation therapy. For example, an implant device may store one or more computer programs that specify waveforms (amplitude, pulse width, frequency, ramp rate, etc.) to be applied across one or more electrodes. Additionally, the implant device may sense brain signals, convert these signals into frequency-domain information, and then use these signals as a controller for stimulation (e.g., amplitude modulation for electronic brain stimulation). Of course, in such systems, neuromodulation therapy implant device must be appropriately programmed for the particular subject. For example, for a relatively simple therapy, such as Parkinson's GPI Deep Brain Stimulation, the implant programming may involve selecting which of multiple electrodes are to be "active" and deliver stimulation, and selecting an amplitude for stimulation to provide an optimal balance of therapeutic effect and side effects.

Programming and reprogramming of implant devices within conventional neuromodulation therapy systems are generally performed in discrete in-clinic programming sessions, during which a clinician manually adjusts the therapy parameters (e.g., active electrodes and amplitudes), dynamically observes and discusses changes in the subject's symptoms, and continue adjusting the implant parameters to find the optimal settings for the subject. However, discrete in-clinic device programming techniques may result in suboptimal and less efficient treatment solutions for several reasons. For example, while some subject symptoms (e.g., tremors) may be easy to identify during an in-person clinic visit, other physical symptoms (e.g., slowness of gait, rigidity) may be more difficult or impossible to detect during the course of a clinic visit. Furthermore, many diseases treatable with neuromodulation therapy, such as Parkinson's disease, Alzheimer's disease, and chronic pain, may present differently throughout the course of a day, based on the subject's fluctuating blood sugar, sleep, medicine consumption, and other cyclical or non-cyclical activity. Such fluctuations cannot practically be measured during a single clinic visit, many clinic visits taking place over a much longer period of time may be needed to determine the subject's optimal parameter set. Additionally, for neuromodulation therapies having more complex anatomical targets (e.g., the subject's hypothalamus), more electrodes (e.g., up to 16 per lead, for 256 bipole combinations of electrodes), more complex programs (e.g., including filters and time delays for closed-loop feedback), and/or more complex biomarkers (e.g., cognition, memory, mood), it may be impossible to determine a subject's optimal therapy configuration from discrete in-person clinic visits and reprogramming.

Further, both neuromodulation therapy implant devices and therapies themselves are becoming increasingly complex. For example, newer implant devices may use up to 16 electrodes per lead, up to four leads to stimulate separate sites, and may support controlling of increasingly more complex waveforms. Thus, there is a need for more complex computation to function as the controller for such systems. However, neuromodulation therapy implant devices may be limited on battery life, and thus the amount of computation that may be performed on these systems also may be limited. For example, processing, memory, and battery restrictions on neuromodulation therapy implant devices may limit the degree to which heavy computation may be performed.

SUMMARY

Embodiments of the present invention generally relate to neuromodulation therapy systems, and more particularly, to simulating neuromodulation therapy.

According to various aspects there is provided methods for updating neuromodulation-therapy algorithms. The methods include: receiving a first dataset corresponding to a particular neuromodulation-therapy implant device; receiving a second dataset corresponding to a particular neuromodulation-therapy algorithm; receiving a third dataset corresponding to a subject-record for a particular subject; determining, based on an execution of a neuromodulation-therapy simulator, one or more predicted performance metrics that is based on the particular neuromodulation-therapy implant device, the particular neuromodulation-therapy algorithm, and the subject-record for the particular subject, wherein the one or more predicted performance metrics correspond to one or more predicted physiological responses of the subject when the particular neuromodulation-therapy algorithm is executed by the particular neuromodulation-therapy implant device to control an electrical output of the particular neuromodulation-therapy implant device; and outputting the one or more predicted performance metrics corresponding to the one or more predicted physiological responses of the subject.

Another aspect of the present disclosure includes a system comprising one or more processors and a non-transitory, computer-readable medium storing instructions, which when executed by one or more processors, cause the one or more processors to perform the method described above.

Another aspect of the present disclosure includes a non-transitory, computer-readable medium storing instructions, which when executed by one or more processors, cause one or more processors to perform the method described above.

DETAILED DESCRIPTION

Figure 1A:
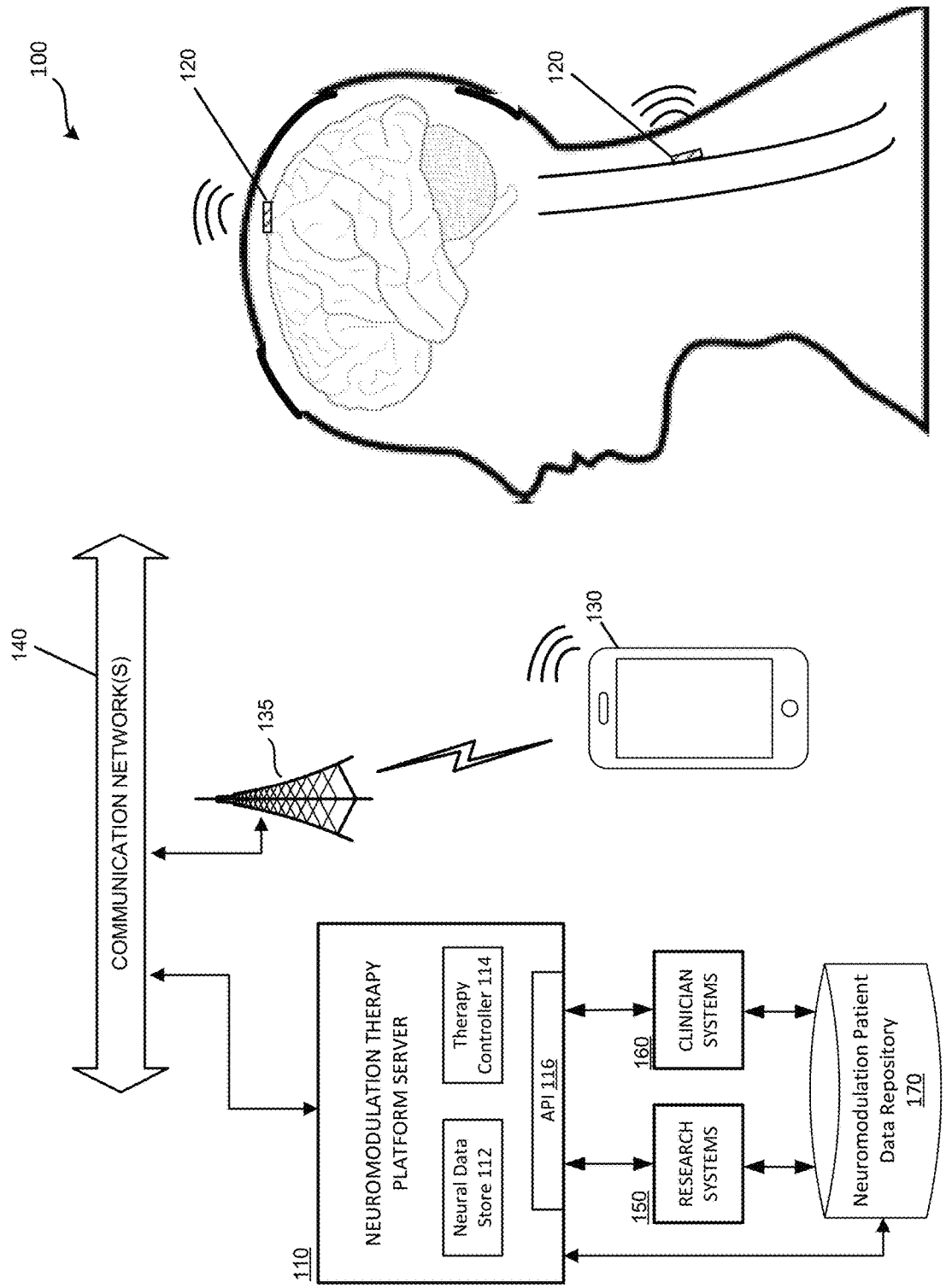
FIG. 1A illustrates an example of a distributed computing environment for providing neuromodulation therapy according to aspects of the present disclosure.

In the following description, for the purposes of explanation, specific details are set forth in order to provide a thorough understanding of various implementations and examples. It will be apparent, however, that various implementations may be practiced without these specific details. For example, circuits, systems, algorithms, structures, techniques, networks, processes, and other components may be shown as components in block diagram form in order not to obscure the implementations in unnecessary detail. The FIGS. and description are not intended to be restrictive.

Some examples, such as those disclosed with respect to the FIGS. in this disclosure, may be described as a process which is depicted as a flowchart, a flow diagram, a data flow diagram, a structure diagram, a sequence diagram, or a block diagram. Although a sequence diagram or a flowchart may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

The processes depicted herein, such as those described with reference to the FIGS. in this disclosure, may be implemented in software (e.g., code, instructions, program) executed by one or more processing units (e.g., processors cores), hardware, or combinations thereof. The software may be stored in a memory (e.g., on a memory device, on a non-transitory computer-readable storage medium). In some examples, the processes depicted in sequence diagrams and flowcharts herein can be implemented by any of the systems disclosed herein. The particular series of processing steps in this disclosure are not intended to be limiting. Other sequences of steps may also be performed according to alternative examples. For example, alternative examples of the present disclosure may perform the steps outlined above in a different order. Moreover, the individual steps illustrated in the FIGS. may include multiple sub-steps that may be performed in various sequences as appropriate to the individual step. Furthermore, additional steps may be added or removed depending on the particular applications. One of ordinary skill in the art would recognize many variations, modifications, and alternatives.

In some examples, each process in the FIGS. of this disclosure can be performed by one or more processing units. A processing unit may include one or more processors, including single core or multicore processors, one or more cores of processors, or combinations thereof. In some examples, a processing unit can include one or more special purpose co-processors such as graphics processors, Digital Signal Processors (DSPs), or the like. In some examples, some or all of the processing units can be implemented using customized circuits, such as Application Specific Integrated Circuits (ASICs), or Field programmable gate arrays (FPGAs)

Various embodiments described herein relate to neuromodulation therapy systems having distributed architectures, in which the neuromodulation therapy implant exists as part of a computing environment having multiple different computers, and potentially multiple different sensors and/or actuators. As described below, such distributed architectures may support additional capabilities including more complex computations for controlling and monitoring neuromodulation therapies, which may lead to more predictable and improved therapy outcomes for subjects (e.g., patients, users or the like).

Referring now to FIG. 1A, an example of a distributed computing environment 100 for providing neuromodulation therapy is illustrated. Distributed computing environment 100 includes one or more implant devices 120 and one or more subject mobile devices 130, which may communicate with one or more neuromodulation therapy platform servers 110 having various storage and computing systems 112-114 for defining, monitoring, and evaluating neuromodulation therapies. Platform servers 110 also may include and/or may be in communication with one or more neuromodulation therapy subject data repositories 170 (which may be internal or external to the platform servers 110), along with research system(s) 150, clinician system(s) 160, and/or various other role-based systems (e.g., subject portals).

As shown in this example, the subject's mobile device(s) 130 (e.g., smartphone, tablet, laptop, smart watch or other wearable computing device, etc.) may connect to the subject's neuromodulation therapy implant device(s) 120, using a network (e.g., near-field communication (NFC), Bluetooth, and/or other short-range wireless communication) and corresponding protocols. A mobile device 130 may be configured to connect to one or more implant devices 120 to receive (e.g., via a push from the implant device(s) 120 or pull from the mobile device 130) data from the implant devices 120 indicating the current state of the therapy (e.g., amplitude, pulse width, frequency, ramp rate, etc.), as well as sensor data collected and/or stored by the implant devices 120 (e.g., that characterize low frequency brain signals, action potentials, motion data, etc.). The sensor data may include raw data collected by one or more electrodes and/or a processed version thereof. For example, sensor data may include the times at which multiple action potentials were detected (e.g., in association with identification of one or more electrodes from which corresponding data was collected and/or in association with an estimated source location of the action potentials). As another example, the sensor data may include the power at each of one or more frequency bands detected within a frequency-domain representation of a signal collected at one or more electrodes. In some embodiments, mobile devices 130 may manage the storing/buffering of this data, as well as transmission of this data to the platform servers 110 and/or directly to a secure data repository 170 over cellular networks 135 (e.g., LTE radio) and/or other communication networks 140. In some cases, the subject's mobile device(s) 130 may aggregate therapy data and/or subject monitoring data received from subject's implant device 120, with additional data from other applications executing on the mobile device 120 and/or data received from other sensors or subject monitoring devices. For instance, a subject's smartphone 130 may receive neuromodulation therapy data from implant devices 120; aggregate that data with location data, motion data, video data, and/or specialized application-based test data collected locally by the smartphone 130; synchronize the aggregated data based on timestamps; and transmit the aggregated and synchronized data to the platform servers 110 or data repository 170.

Within the platform servers 110, and/or within the data repositories 170, the data received from the subject's implant device(s) 120 and/or mobile device(s) 130 may be used to drive processes which may determine new sets of therapy parameters to be loaded onto the subject's implant 120. The newly determined sets of parameters then may be pushed from the platform servers 110 and/or data repositories 170 to the subject's mobile device 130. Either in response to receiving new sets of neuromodulation therapy parameters, and/or at predetermined time intervals, the subject's mobile device 130 may then push the new parameters to the implant device(s) 120. (In some instances, an implant device 120 may alternatively or additionally pull the new parameters. The implant device 120 may request parameter updates, for example, at routine time periods, in response to detecting particular neural-data signatures or trends, in response to detecting an environmental or stimulus condition, etc.) The implant device 120 may receive the new neuromodulation therapy parameters (for example) via a secure short-range radio (e.g., Bluetooth) connection, and the parameters can then be used to update and/or reprogram the neuromodulation therapy delivered by the implant device 120 on-the-fly.

Platform servers 110 may include various servers and/or subsystems 112-114 for receiving and processing neuromodulation therapy data and/or subject monitoring data, determining new parameters for specific subjects and implant devices, selecting neuromodulation therapy algorithms for specific subject therapies, supporting the design and implementation of new neuromodulation therapy algorithms, and the like. In some embodiments, platform servers 110 (and/or data repositories 170) may be implemented within a secure cloud service platform (and thus in some cases the servers 110 may be referred as cloud platform therapy servers 110). Such cloud-based implementations may provide advantages for rapid scalability of computing resources when needed, to allow the platform servers 110 to design, implement, and execute complex neuromodulation therapy algorithms, including machine-learning algorithms, process data and train models using large-scale neuromodulation therapy subject data sets from repositories 170, etc. However, in other embodiments, one or both of the platform servers 110 and the data repositories need not be implemented within a cloud computing environment, but instead may use a standalone dedicated computing infrastructure.

In this example, a neuromodulation therapy platform may include a neural data store 112, a therapy controller 114, and one or more application programming interfaces (APIs) 116. The neural data store 112 may include one or more databases configured to store and analyze neuromodulation therapy data and related subject data. For example, a neural data store 112 may be implemented as a time-series database for storing voltage waveform, processed versions thereof (e.g., identifying times and/or counts of action potentials, power of neural signals within one or more frequency bands and/or phase data) and motion data from the implant, plus a relational database for storing subject data (e.g., subject identifiers, therapy configuration data, data consent graphs, etc.). The therapy controller 114 may be configured to identify and effect particular specifications and/or parameters for a therapy to be administered. For example, the therapy controller 114 may be configured to identify how frequently a stimulation is to be administered (and/or a trigger for administering a stimulation), a temporal pattern of a stimulation, an envelope of a stimulation, and/or one or more amplitudes of a stimulation. The therapy controller 114 need not itself independently determine these parameters but may instead identify the parameters based on a communication received from the mobile device 130. The mobile device 130 also need not (though it may) independently determine these parameters but may instead identify the parameters based on a communication received from a remote device that is associated with a service (e.g., a cloud-based service). The therapy controller service 114 (and/or the mobile phone 130 and/or a remote server) may analyze current and historical data from the subject in order to determine when the subject's therapy parameters should be updated, and to calculate the new sets of updated therapy parameters for the subject. The service 114 also may push these new parameter sets to the subject's mobile device 130, which in turn may push the new therapy parameters to the subject's implant 120. As discussed below, in various embodiments this process may iterate repeatedly, continuously and/or on different time scales for different therapy parameters. Finally, API(s) 116 may allow clinicians, researchers, and users of other roles with functionalities and data access to which they have consented use for. As discussed below, the consented data access may be stored and tracked via subject consent graphs. Various graphical interfaces and/or web-based application interfaces may be configured to use APIs 116 to access the subject data and/or to provide functionality to create or modify therapy algorithms.

Figure 1B:
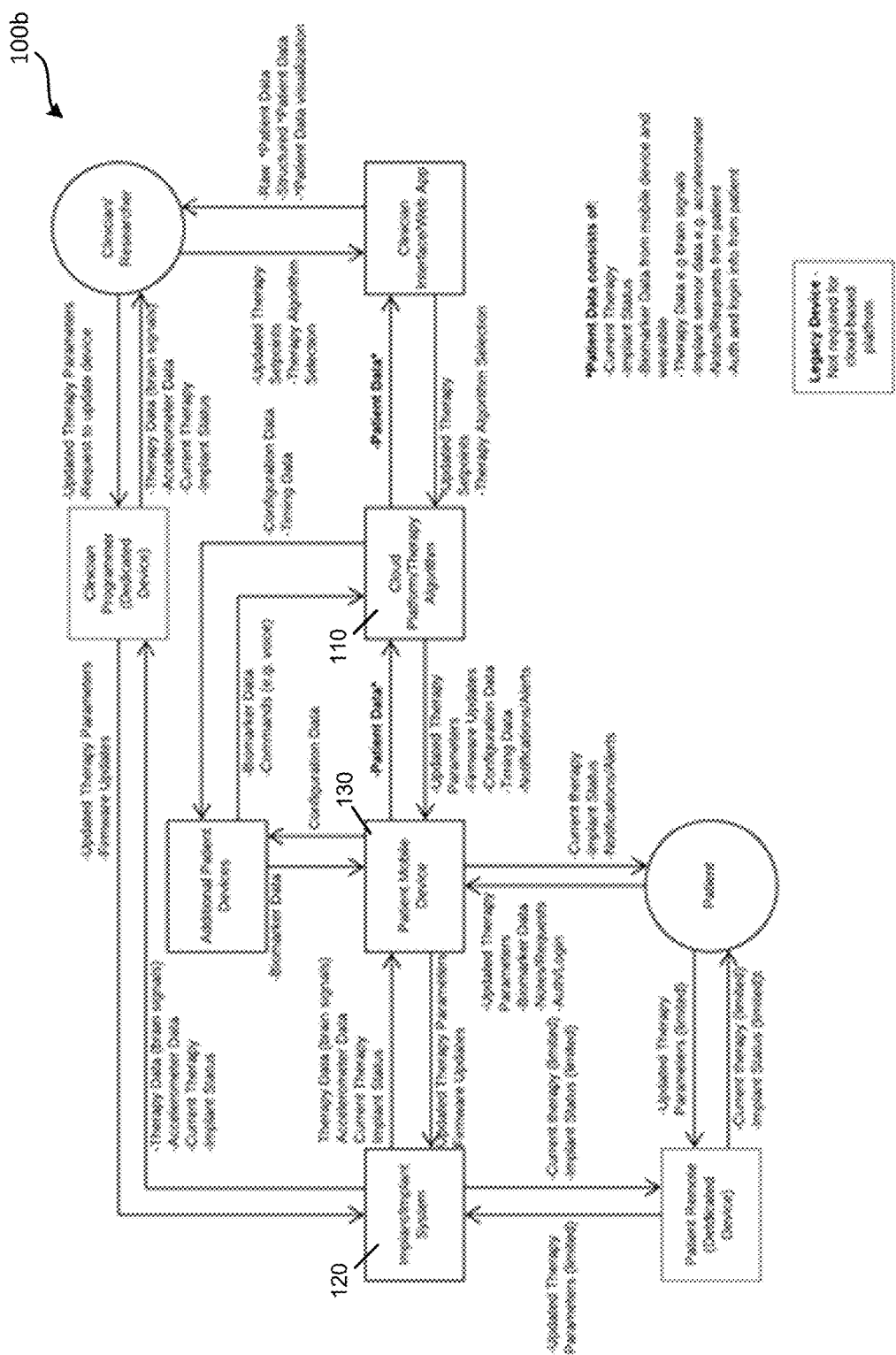
FIG. 1B illustrates another example of a distributed computing environment for providing neuromodulation therapy according to aspects of the present disclosure.

Referring briefly to FIG. 1B, another example is shown of a distributed computing environment 100*b* for providing neuromodulation therapy. The distributed system 100*b* in this example may correspond to a specific implementation of the distributed computing environment discussed above in FIG. 1A. In this example, several of the specific entities/components are identified (e.g., Subject Mobile Device, Implant Device, Subject Remote, Additional Subject Devices, Cloud Platform/Therapy Algorithm, Clinician/Researcher, Clinician Programmer Device, Clinician Interface/Web App, Cloud Platform/Therapy Algorithm, and/or Legacy Device(s)) for a specific implantation of a distributed neuromodulation therapy system, along with the data flows showing the specific data transmissions between entities/components.

In the example environment 100*b*, the implant system may have bi-directional communication with any of three separate devices: the subject's mobile device (e.g., 130), a subject dedicated remote control device, and/or a dedicated clinician programmer device. From any or all of these devices, the implant system may receive updated therapy parameters and/or firmware. Additionally, the implant system may transmit out to any of these devices data including subject therapy data (e.g., brain signals, biomarkers, etc.), accelerometer data or other movement data from sensors within the implant, current therapy data (e.g., the current parameter set), and/or implant status data (e.g., operational status, errors, current power level, etc.). The subject's mobile device 130 may interact with the platform server 110 executing the subject's therapy algorithm, and may receive from the platform server 110 the updated therapy parameters and firmware to be provided to the implant system 120, as well as configuration data (e.g., for configuring the monitoring/biomarker detection performed by additional subject devices), timing data (e.g., to control timing of data transmissions to and from the implant device 120), and notifications/alerts to be presented to the subject via mobile device 130. The subject's mobile device 130 also may interact with one or more additional subject devices, several examples of which are described below in reference to FIGS. 2A and 2B. Additional subject devices may be configured, e.g., using configuration data received from the platform sever 110 and/or based on configuration settings provided by the subject or clinician, to externally monitor certain subject characteristics, activities, and/or biomarkers.

In some embodiments, in addition to the neuromodulation therapy systems 100 described above, it may be valuable to incorporate additional subject monitoring devices to detect and monitor the subject's biomarkers, symptoms, and side effects. For instance, while detecting a subject's illnesses or other conditions, and while administering and modifying neuromodulation therapies for the subject, it may be useful to monitor subject behaviors and activities that cannot easily and consistently be detected during clinical visits, such as increases or decreases in the subject's tremors, rigidity, dystonia, gait smoothness, etc. Additional subject monitoring may be useful to track the subject's sleep patterns and disruptions, food and drink consumption, medication usage, exercise patterns, and the like.

Figure 2A:
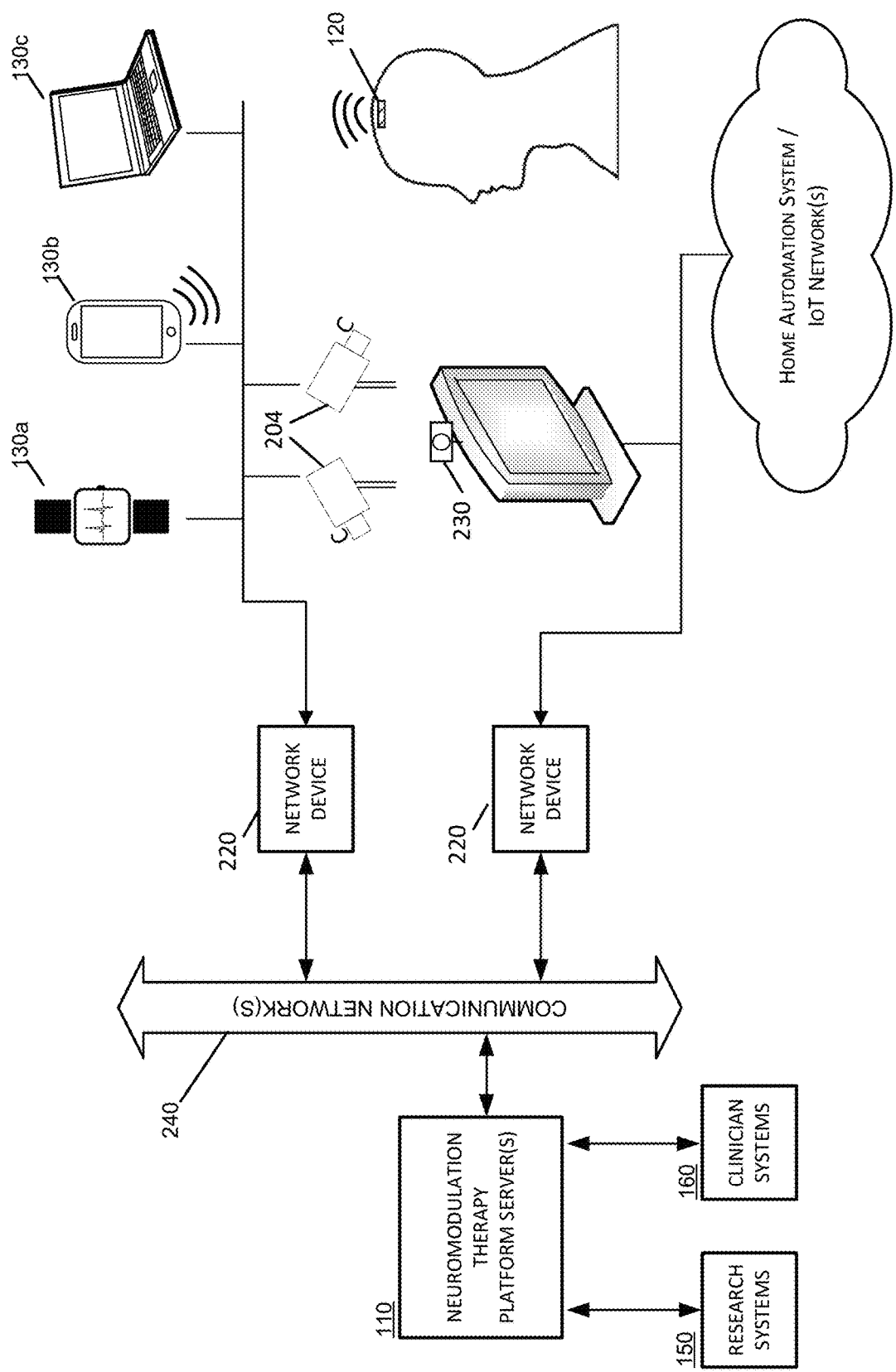
FIG. 2A and FIG. 2B illustrate examples of neuromodulation therapy systems according to aspects of the present disclosure.
Figure 2B:
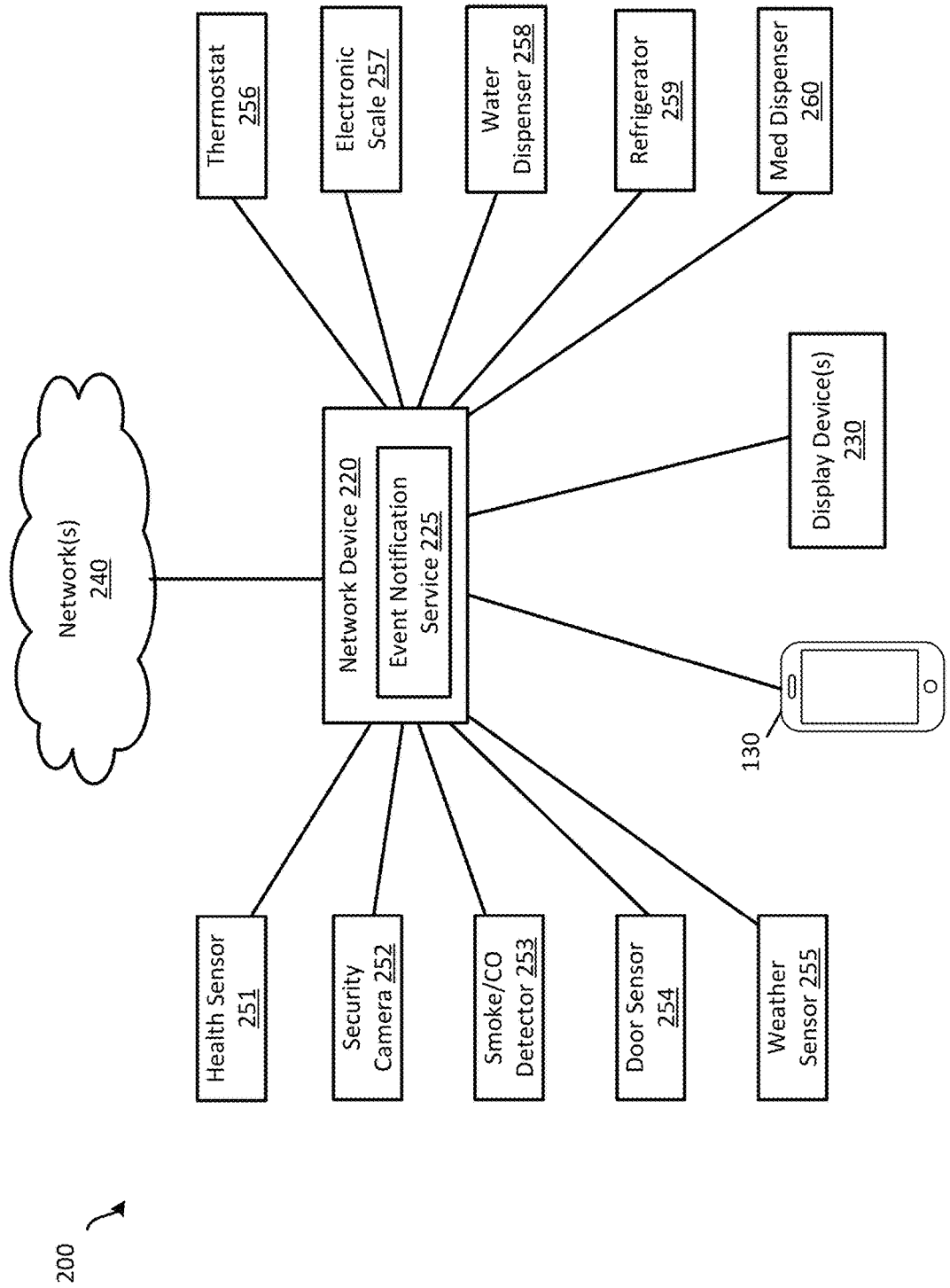

Accordingly, FIGS. 2A and 2B show further examples of neuromodulation therapy systems which include various devices configured to monitor the behaviors and activities of the subject. For example, as shown in FIG. 2A, a subject having a neuromodulation therapy implant device 120, may also be associated with one or more mobile devices 130 configured to communicate with the implant device 120 to receive neuromodulation therapy data, brain signals and other subject monitoring data, and package/transmit the combined data to the neuromodulation therapy platform servers 110. In this example, the subject's smartphone 130*b* may be configured to communicate with the subject's implant device 120, but in other cases the interface to the implant 120 may be the subject's smart watch 130*a* and/or other personal computing devices 130*c*.

Additionally, each of these subject mobile devices 130 also may be used in conjunction to monitor subject activities and behaviors. Such monitoring may depend on the capabilities and sensors of each device. For example, the subject's smart watch 130*a* may monitor the subject's activity levels, heart rate, gait length and smoothness, sleep patterns, etc. The subject's smartphone 130*b* may monitor some or all of the same subject activities and behaviors, as well as the location of the subject (e.g., using a GPS receiver, Wifi, etc.), current environmental conditions (e.g., weather, temperature, pressure, light conditions, background noise conditions, etc.), and user movement (e.g., using an accelerometer, GPS receiver, etc.). Additional computing devices, such as personal computers 130*c*, may be used to monitor some or all of the same or similar user behaviors, as well as additional data may such as the subject's eye movement patterns, dexterity, typing accuracy and efficiency, etc.

Besides the subject's mobile computing devices 130, one or more networks of additional devices may be configured to perform subject monitoring and transmit subject monitoring data back to the neuromodulation therapy platform servers 110. For example, as shown in FIG. 2A, one or more cameras 204 and 230 may be used to visually monitor the subject to detect various subject data relating to tremors, rigidity, dystonia, gait, sleep data, food and drink consumption, medication usage, exercise patterns, stressful events or activities, etc. In addition to cameras 202/230, and the subject's personal mobile devices 130, any number of additional electronic sensors or appliances may be used to track the subjects activities and behaviors, and transmit that data to the platform servers 110.

For example, referring briefly to FIG. 2B, a network of additional monitoring devices is shown that may work independently or in conjunction with the neuromodulation therapy system of FIG. 2A, to detect subject behavior and activity data that may be relevant to the subject's neuromodulation therapy. The network of devices shown in FIG. 2B may correspond to a home automation system (HAS) of devices, an Internet-of-Things (IoT) device network, or the like. The specific subject monitoring devices shown in FIG. 2B are illustrative only, and it should be understood that various subsets and/or different monitoring devices may be used in other examples. Health sensor 251 may support monitoring of one or more vital characteristics of the subject, such as heart rate, respiration, blood pressure, blood sugar, etc. In some cases, health monitor 251 may include a button or other actuator that the subject can use to request medical assistance. Security cameras 252 may be similar or identical to cameras 204/230 discussed above, and may be configured to monitor the subject's movements for detection of activities and exercise patterns, as well as detection of tremors, rigidity, dystonia, changes in gait, sleep patterns, etc. Smoke and/or CO detectors 253 may detect incidents or alarms that have occurred at the subject's location, as well as certain quality of the air and environment (e.g., CO, second-hand smoke, radon, etc.). Door sensors 254 may be used to detect when the subject leaves and returns a particular location, when the subject receives visitors, etc. Weather sensors 255 may detect various forms of environmental data, including local or non-local ambient temperature, humidity, wind speed, barometric pressure, etc. Thermostat 256 may detect temperature data and the initiation of heating/cooling commands by the subject. Electronic scale 257 may be configured to record the subject's weight measurements and corresponding times. Additionally, water dispensers 258 and/or refrigerator appliance controllers 259 (and/or other kitchen appliances) may be configured to determine the subject's nutritional consumption. Similarly, one or more electronic medication dispensers 260 may collect and analyze data relating to the subject's use of medications, and may include devices such as electronic pill dispensers, insertable or embedded medical devices such as computerized intravenous (IV) drip devices, and/or other automated medication dispensing devices.

Any or all of the subject monitoring devices used in connection with neuromodulation therapy systems, such as those shown in FIGS. 2A and 2B, may be configured to transmit their data to the platform servers 110, via network devices 220 (e.g., routers and intermediary network components). Such transmissions may be made either directly or indirectly via the subject's computing devices 130. Additionally, in some embodiments, neuromodulation therapy platform servers 110 may be configured to provide notifications to the subject, using an event notification system 225 and/or mobile applications executing on the subject's devices 130. Such notifications may be include instructions or reminders from the platform servers 110 directing the subject perform a particular activity (e.g., taking medication, required sleep or exercise, perform self-diagnostics for symptoms/side effects/biomarkers, etc.). Additional notifications may be used to inform the subject and/or obtain consent for a modification to the subject's neuromodulation therapy algorithm or parameters.

Figure 3A:
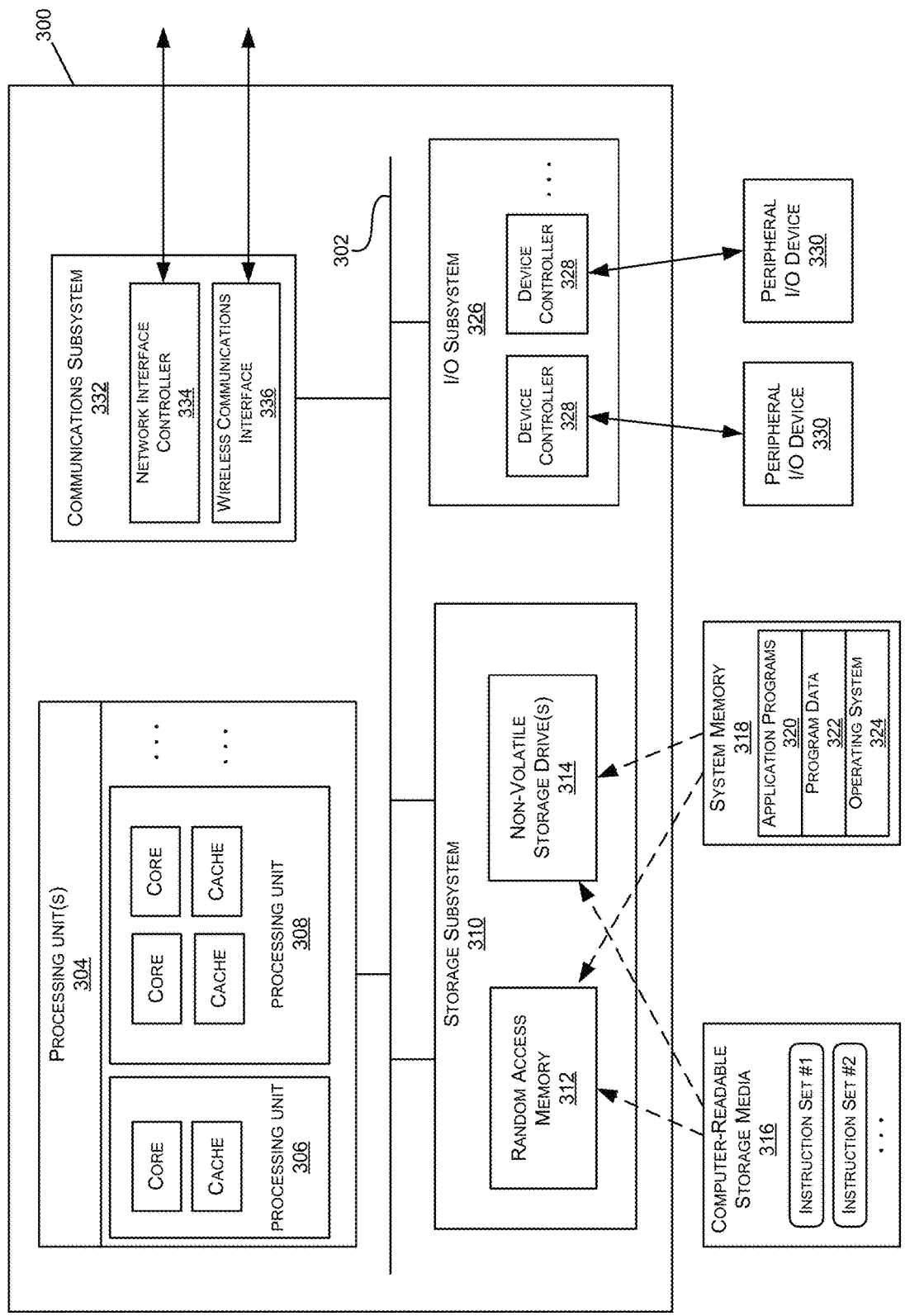
FIG. 3A is a block diagram of an illustrative computer system according to aspects of the present disclosure.

With reference now to FIG. 3A, a block diagram of an illustrative computer system is shown. The system 300 may correspond to any of the computing devices or servers of the neuromodulation therapy systems 100 described above, or any other computing devices described herein. In this example, computer system 300 includes processing units 304 that communicate with a number of peripheral subsystems via a bus subsystem 302. These peripheral subsystems include, for example, a storage subsystem 310, an I/O subsystem 326, and a communications subsystem 332.

Bus subsystem 302 provides a mechanism for letting the various components and subsystems of computer system 300 communicate with each other as intended. Although bus subsystem 302 is shown schematically as a single bus, alternative embodiments of the bus subsystem may utilize multiple buses. Bus subsystem 302 may be any of several types of bus structures including a memory bus or memory controller, a peripheral bus, and a local bus using any of a variety of bus architectures. Such architectures may include, for example, an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard.

Processing unit 304, which may be implemented as one or more integrated circuits (e.g., a conventional microprocessor or microcontroller), controls the operation of computer system 300. One or more processors, including single core and/or multicore processors, may be included in processing unit 304. As shown in the figure, processing unit 304 may be implemented as one or more independent processing units 306 and/or 308 with single or multicore processors and processor caches included in each processing unit. In other embodiments, processing unit 304 may also be implemented as a quad-core processing unit or larger multicore designs (e.g., hexa-core processors, octo-core processors, ten-core processors, or greater. As discussed above, in some cases, processing unit 304 may include one or more specialized ASICs designed and configured for cryptocurrency mining and/or specialized cryptographic hardware for handling cryptocurrency transactions.

Processing unit 304 may execute a variety of software processes embodied in program code, and may maintain multiple concurrently executing programs or processes. At any given time, some or all of the program code to be executed can be resident in processor(s) 304 and/or in storage subsystem 310. In some embodiments, computer system 300 may include one or more specialized processors, such as digital signal processors (DSPs), outboard processors, graphics processors, application-specific processors, and/or the like.

I/O subsystem 326 may include device controllers 328 for one or more user interface input devices and/or user interface output devices 330. User interface input and output devices 330 may be integral with the computer system 300 (e.g., integrated audio/video systems, and/or touchscreen displays), or may be separate peripheral devices which are attachable/detachable from the computer system 300.

Input devices 330 may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. Input devices 330 may also include three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additional input devices 630 may include, for example, motion sensing and/or gesture recognition devices that enable users to control and interact with an input device through a natural user interface using gestures and spoken commands, eye gesture recognition devices that detect eye activity from users and transform the eye gestures as input into an input device, voice recognition sensing devices that enable users to interact with voice recognition systems through voice commands, medical imaging input devices, MIDI keyboards, digital musical instruments, and the like.

Output devices 330 may include one or more display subsystems, indicator lights, or non-visual displays such as audio output devices, etc. Display subsystems may include, for example, cathode ray tube (CRT) displays, flat-panel devices, such as those using a liquid crystal display (LCD) or plasma display, light-emitting diode (LED) displays, projection devices, touch screens, and the like. In general, use of the term "output device" is intended to include all possible types of devices and mechanisms for outputting information from computer system 300 to a user or other computer. For example, output devices 330 may include, without limitation, a variety of display devices that visually convey text, graphics and audio/video information such as monitors, printers, speakers, headphones, automotive navigation systems, plotters, voice output devices, and modems.

Computer system 300 may comprise one or more storage subsystems 310, comprising hardware and software components used for storing data and program instructions, such as system memory 318 and computer-readable storage media 316. The system memory 318 and/or computer-readable storage media 316 may store program instructions that are loadable and executable on processing units 304, as well as data generated during the execution of these programs.

Depending on the configuration and type of computer system 300, system memory 318 may be stored in volatile memory (such as random access memory (RAM) 312) and/or in non-volatile storage drives 314 (such as read-only memory (ROM), flash memory, etc.) The RAM 312 may contain data and/or program modules that are immediately accessible to and/or presently being operated and executed by processing units 304. In some implementations, system memory 318 may include multiple different types of memory, such as static random access memory (SRAM) or dynamic random access memory (DRAM). In some implementations, a basic input/output system (BIOS), containing the basic routines that help to transfer information between elements within computer system 300, such as during start-up, may typically be stored in the non-volatile storage drives 314. By way of example, and not limitation, system memory 318 may include application programs 320, such as client applications, Web browsers, mid-tier applications, server applications, etc., program data 322, and an operating system 324.

Storage subsystem 310 also may provide one or more tangible computer-readable storage media 316 for storing the basic programming and data constructs that provide the functionality of some embodiments. Software (programs, code modules, instructions) that when executed by a processor provide the functionality described herein may be stored in storage subsystem 310. These software modules or instructions may be executed by processing units 304. Storage subsystem 310 may also provide a repository for storing data used in accordance with the present invention.

Storage subsystem 310 may also include a computer-readable storage media reader that can further be connected to computer-readable storage media 316. Together and, optionally, in combination with system memory 318, computer-readable storage media 316 may comprehensively represent remote, local, fixed, and/or removable storage devices plus storage media for temporarily and/or more permanently containing, storing, transmitting, and retrieving computer-readable information.

Computer-readable storage media 316 containing program code, or portions of program code, may include any appropriate media known or used in the art, including storage media and communication media, such as but not limited to, volatile and non-volatile, removable and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media. This can also include nontangible computer-readable media, such as data signals, data transmissions, or any other medium which can be used to transmit the desired information and which can be accessed by computer system 300.

By way of example, computer-readable storage media 316 may include a hard disk drive that reads from or writes to non-removable, nonvolatile magnetic media, a magnetic disk drive that reads from or writes to a removable, non-volatile magnetic disk, and an optical disk drive that reads from or writes to a removable, nonvolatile optical disk such as a CD ROM, DVD, and Blu-Ray® disk, or other optical media. Computer-readable storage media 316 may include, but is not limited to, Zip® drives, flash memory cards, universal serial bus (USB) flash drives, secure digital (SD) cards, DVD disks, digital video tape, and the like. Computer-readable storage media 316 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 300.

Communications subsystem 332 may provide a communication interface from computer system 300 and external computing devices via one or more communication networks, including local area networks (LANs), wide area networks (WANs) (e.g., the Internet), and various wireless telecommunications networks. As illustrated in FIG. 3A, the communications subsystem 332 may include, for example, one or more network interface controllers (NICs) 334, such as Ethernet cards, Asynchronous Transfer Mode NICs, Token Ring NICs, and the like, as well as one or more wireless communications interfaces 336, such as wireless network interface controllers (WNICs), wireless network adapters, and the like. Additionally and/or alternatively, the communications subsystem 332 may include one or more modems (telephone, satellite, cable, ISDN), synchronous or asynchronous digital subscriber line (DSL) units, FireWire® interfaces, USB® interfaces, and the like. Communications subsystem 336 also may include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 802.11 family standards, or other mobile communication technologies, or any combination thereof), global positioning system (GPS) receiver components, and/or other components.

The various physical components of the communications subsystem 332 may be detachable components coupled to the computer system 300 via a computer network, a FireWire® bus, or the like, and/or may be physically integrated onto a motherboard of the computer system 300. Communications subsystem 332 also may be implemented in whole or in part by software.

In some embodiments, communications subsystem 332 may also receive input communication in the form of structured and/or unstructured data feeds, event streams, event updates, and the like, on behalf of one or more users who may use or access computer system 300. For example, communications subsystem 332 may be configured to receive data feeds in real-time from users of social networks and/or other communication services, web feeds such as Rich Site Summary (RSS) feeds, and/or real-time updates from one or more third party information sources. Additionally, communications subsystem 332 may be configured to receive data in the form of continuous data streams, which may include event streams of real-time events and/or event updates (e.g., sensor data applications, financial tickers, network performance measuring tools, clickstream analysis tools, etc.). Communications subsystem 332 may output such structured and/or unstructured data feeds, event streams, event updates, and the like to one or more data stores that may be in communication with one or more streaming data source computers coupled to computer system 300.

Due to the ever-changing nature of computers and networks, the description of computer system 300 depicted in the FIG. is intended only as a specific example. Many other configurations having more or fewer components than the system depicted in the FIG. are possible. For example, customized hardware might also be used and/or particular elements might be implemented in hardware, firmware, software, or a combination. Further, connection to other computing devices, such as network input/output devices, may be employed. Based on the disclosure and teachings provided herein, a person of ordinary skill in the art will appreciate other ways and/or methods to implement the various embodiments.

Figure 3B:
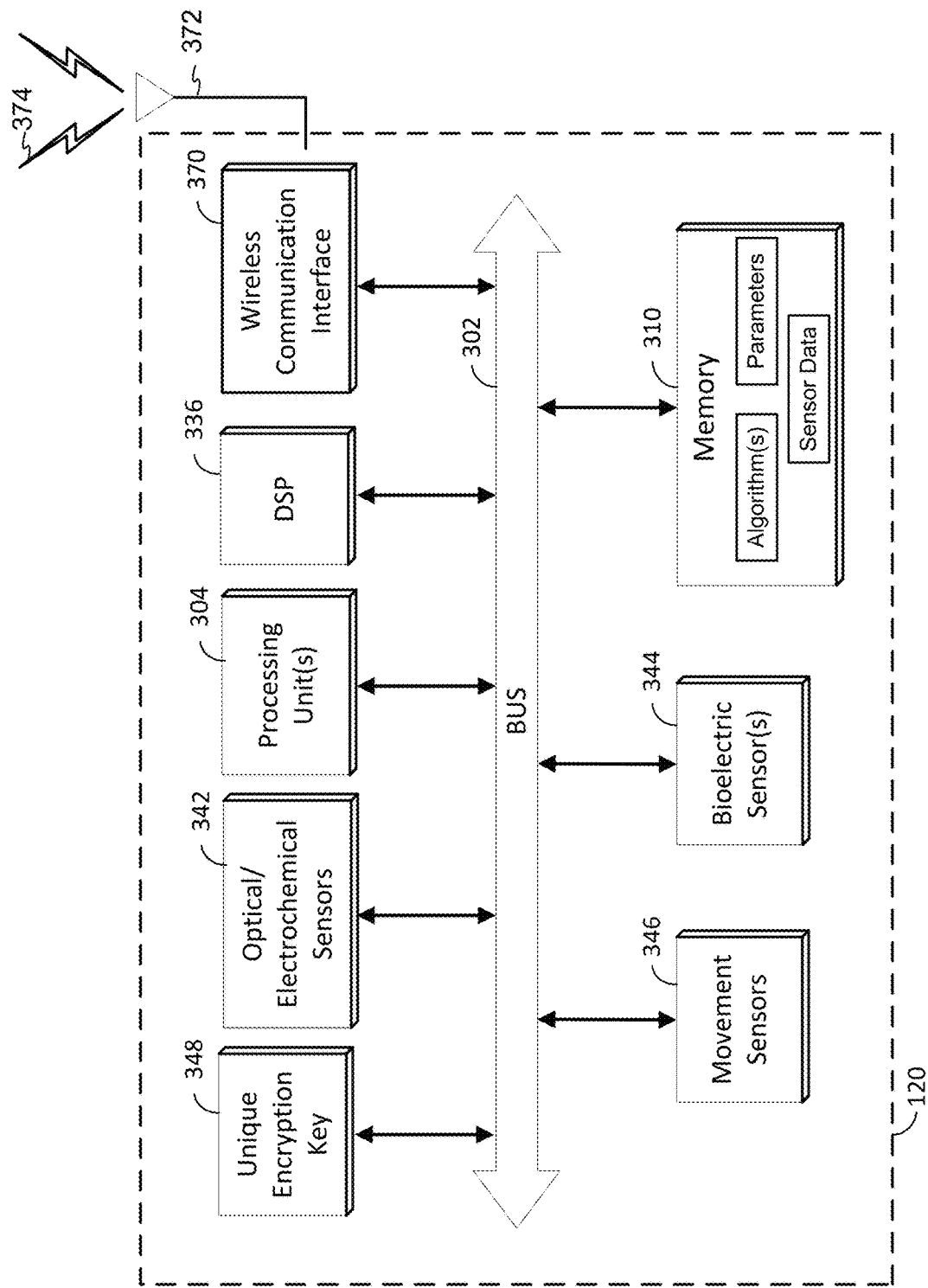
FIG. 3B is a block diagram of an example neuromodulation therapy implant device according to aspects of the present disclosure.

Referring now to FIG. 3B, a block diagram is shown illustrating the component of an example neuromodulation therapy implant device 120. As noted above, implant devices 120 may be configured to execute subject-specific programming in order to deliver electrical stimulation to specific target areas within the brain or nervous system of the subject. The electrical stimulation may be delivered by the implant 120 using electrodes, in accordance with specified waveforms (e.g., amplitudes, pulse widths, frequencies, ramp rates, etc.). The implant device 120 shown in FIG. 3B may comprise hardware elements that can be electrically coupled via a bus 302 (or may otherwise be in communication, as appropriate). The hardware elements may include a processing unit(s) 304 which may comprise without limitation one or more general-purpose processors, one or more special-purpose processors (such as digital signal processing (DSP) chips, graphics acceleration processors, application specific integrated circuits (ASICs), and/or the like), and/or other processing structure or means, which can be configured to perform one or more of the methods described herein. As shown in FIG. 3B, some embodiments may have a separate DSP 336, depending on desired functionality.

Implant devices 120 may also include wireless communication interfaces 370, which may comprise without limitation an infrared communication devices, wireless communication devices, and/or a chipset (such as a Bluetooth® device, an IEEE 802.11 device, an IEEE 802.15.4 device, a Wi-Fi device, a WiMax device, cellular communication facilities, etc.), and/or the like, which may enable the implant 120 to communicate via wireless networks and Radio Access Technology (RAT) networks described above with regard to FIGS. 1-2. The wireless communication interface 370 may permit data to be communicated with the subject's mobile devices 130, as well as other networks, wireless access points, wireless base stations, other computer systems, and/or any other electronic devices described herein. The communication can be carried out via one or more wireless communication antenna(s) 372 that send and/or receive wireless signals 374.

Depending on desired functionality, the wireless communication interface 370 may comprise separate transceivers to communicate with base stations (e.g., eNBs) and other terrestrial transceivers, such as wireless devices and access points, belonging to or associated with one or more wireless networks. These wireless networks may comprise various network types. For example, a WWAN may be a CDMA network, a Time Division Multiple Access (TDMA) network, a Frequency Division Multiple Access (FDMA) network, an Orthogonal Frequency Division Multiple Access (OFDMA) network, a Single-Carrier Frequency Division Multiple Access (SC-FDMA) network, a WiMax (IEEE 802.16) network, and so on. A CDMA network may implement one or more radio access technologies (RATs) such as cdma2000, Wideband CDMA (WCDMA), and so on. Cdma2000 includes IS-95, IS-2000, and/or IS-856 standards. A TDMA network may implement GSM, Digital Advanced Mobile Phone System (D-AMPS), or some other RAT. An OFDMA network may employ LTE, LTE Advanced, NR and so on. LTE, LTE Advanced, NR, GSM, and WCDMA are described (or being described) in documents from 3GPP. Cdma2000 is described in documents from a consortium named "3rd Generation Partnership Project 2" (3GPP2). 3GPP and 3GPP2 documents are publicly available. A WLAN may also be an IEEE 802.11x network, and a WPAN may be a Bluetooth network, an IEEE 802.15x, or some other type of network. The techniques described herein may also be used for any combination of WWAN, WLAN and/or WPAN.

The implant device 120 may further include various sensor(s) for detecting brain/nervous system activity of the subject, including optical/electrochemical sensors 342 and/or bioelectric sensors 344 used to detect brain signals. In some embodiments, the implant device 120 also may include movement sensors 346 for tracking subject movement. Additionally, as discussed below in more detail, the implant 120 may include one or more unique encryption keys 348 stored securely within the memory of the implant 120, which may be used to assure secure communications to and from the implant 120, as well as for secure pairing of the implant 120 with the subject's other personal computing devices 130.

The implant device 120 may further include a memory 310. The memory 310 may comprise, without limitation, local storage, a disk drive, an optical storage device, a solid-state storage device, such as a random access memory ("RAM"), and/or a read-only memory ("ROM"), which can be programmable, flash-updateable, and/or the like. Such storage devices may be configured to implement any appropriate data stores, including without limitation, various file systems, database structures, and/or the like. The memory 310 may be used, among other things, to store and execute neuromodulation therapy algorithms and parameter sets, store sensor data received from sensors 342, 344, 346, using a database, linked list, or any other type of data structure. In some embodiments, wireless communication interface 370 may additionally or alternatively comprise memory.

The memory 310 of implant device 120 also may comprise software elements (not shown), including an operating system, device drivers, executable libraries, and/or other code, such as one or more application programs, which may comprise computer programs provided by various embodiments, and/or may be designed to implement methods, and/or configure systems, provided by other embodiments, as described herein. Merely by way of example, one or more procedures described with respect to the functionality for implant device 120 discussed above might be implemented as code and/or instructions executable by implant device 120 (and/or a processing unit within the implant device 120). In an aspect, then, such code and/or instructions can be used to configure and/or adapt a general purpose computer (or other device) to perform one or more operations in accordance with the described methods.

I. Neuromodulation Therapy Monitoring and Continuous Therapy Reprogramming

Certain aspects described herein relate to performing continuous programming and reprogramming of subject-specific neuromodulation therapies, rather than discrete programming for neuromodulation therapy implant devices. In some embodiments, a neuromodulation therapy platform 110 and distributed computing environment 100 may be configured to allow for neuromodulation algorithms and/or parameters to be continuously adapted and optimized, based on data sensed or detected by the subject's implant device 120 and/or based on data and/or discrete data from other data sources. Continuous streams of data may be received from the one or more electrodes of the implant device 110, the subject's mobile devices 130, from the subject himself/herself (e.g., feedback data provided via the subject's mobile device 130), and/or from any of the various subject monitoring devices described in reference to FIGS. 2A-2B. The incoming data may be received and analyzed by one or more of the subject implant device 120, user device(s) 130, platform server(s) 110, and/or research or clinician system(s) 150-160, to automatically update the subject's neuromodulation therapy at any time.

Figure 4:
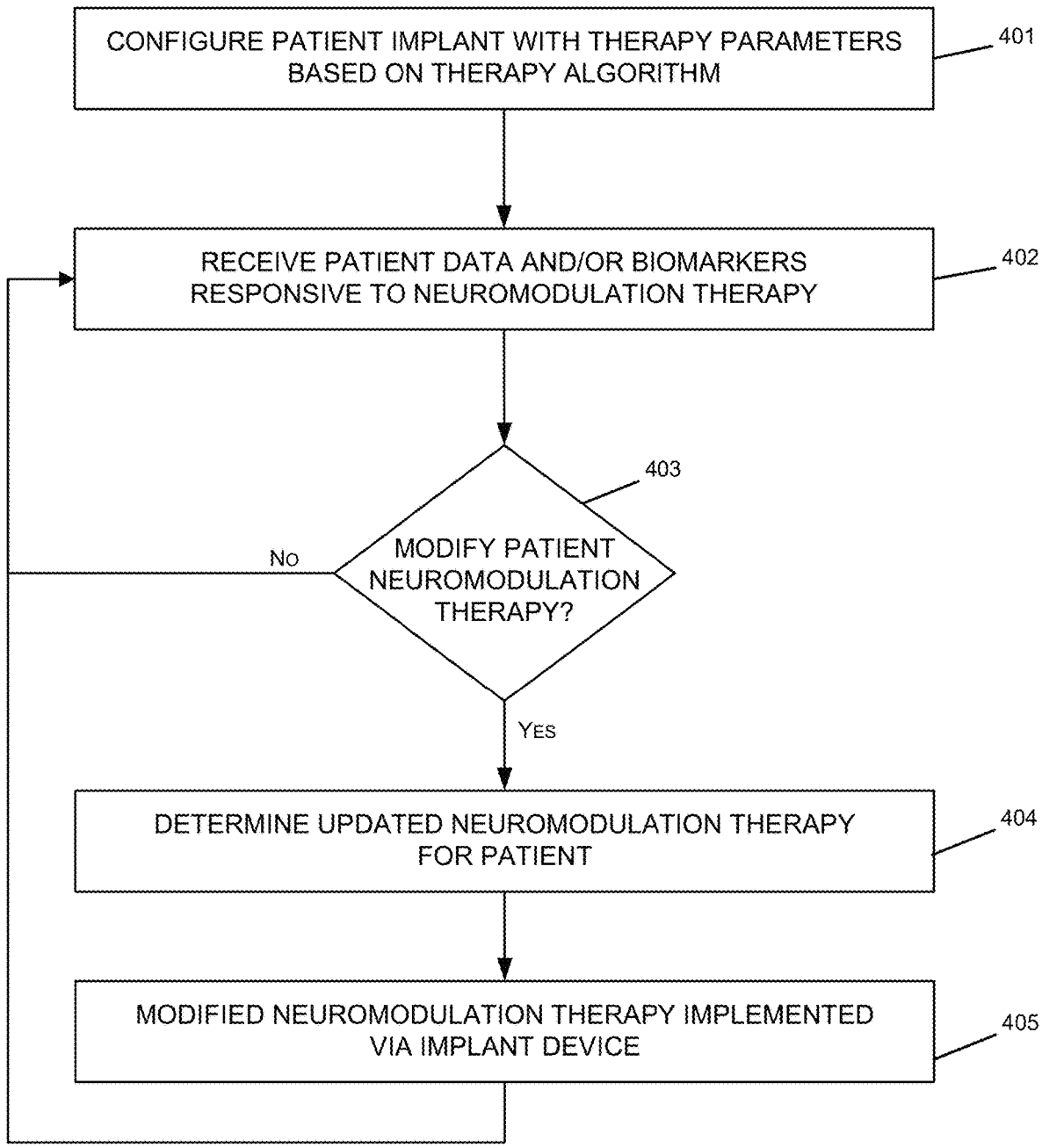
FIG. 4 is a flowchart of an example process for continuous monitoring and modification of a subject's neuromodulation therapy according to aspects of the present disclosure.

Referring now to FIG. 4, a flowchart is shown illustrating an example process for continuous monitoring and modification of a subject's neuromodulation therapy. As described below in reference to FIGS. 5A-5C, continuous neuromodulation therapy and reprogramming may be performed using one or a combination of multiple different techniques operating at the various devices within a distributed computing environment 100. Thus, FIG. 4 represents a high-level process flowchart only, and need not be tied to any particular devices with the neuromodulation therapy environment 100.

In step 401, a neuromodulation therapy implant device 120 is configured with a set of therapy parameters that the implant 120 may be used to administer the neuromodulation therapy to the subject. In some cases, the set of neuromodulation therapy parameters may be determined by the execution of a neuromodulation therapy algorithm. As used herein, neuromodulation therapy parameters may refer to a set of parameters loaded onto an implant device 120 and controlling the administration of the neuromodulation therapy stimulation delivered to the subject by the implant device 120. For an electrical neuromodulation therapy implant device 120, examples of neuromodulation therapy parameters may include data defining the electrode configurations of the implant 120 (e.g., anode/cathode configurations), stimulation amplitudes, stimulation frequencies, stimulation pulse widths, and stimulation duty cycles, etc. In some embodiments, particularly in closed-loop systems where the implant device 120 may perform brain signal monitoring and/or other subject biomarker monitoring, the implant device 120 may store additional neuromodulation therapy parameters, such as sampling rates for the implant's sensors, filter parameters for data acquisition systems, telemetry timing data, Linear Discriminant Analysis (LDA) data, and/or any other computational parameters for the computations performed by the implant device 120. The neuromodulation therapy parameters may transmitted to the implant device 120 via the subject's mobile device be stored within the on-device registers of the implant device 120.

In some cases, the therapy parameters may be an initial set of parameters preconfigured into the neuromodulation therapy algorithm, which define the characteristics of the neuromodulation therapy stimulation that will be initially delivered to the subject. However, in other cases, the neuromodulation therapy algorithm may be initialized with a null set of stimulation parameters, and the implant device 120 may be configured to initially operate in a "record only" mode in which no neuromodulation therapy stimulation is provided until after an initial period of monitoring and analyzing the brain signals/biomarkers detected from the subject.

In contrast, as used herein, a neuromodulation therapy algorithm may refer to executable software program configured to analyze incoming neuromodulation therapy data and determine updates to one or more sets of neuromodulation therapy parameters. In some embodiments, therapy algorithms may be implemented in higher level programming languages (e.g., Python), and may be stored and executed within platform servers 110. However, in some cases it may be possible for a therapy algorithm to execute within a subject's mobile device 130 or other personal computing device (e.g., personal computer, neuromodulation therapy remote control, etc.). Inputs to a subject-specific implementation of a neuromodulation therapy algorithm may include streams of incoming therapy data and/or discrete sets of incoming therapy data for the subject (e.g., current parameter sets, biomarkers, subject brain signals, subject monitoring data from the subject's mobile device 130 and/or other external sensors/devices, etc.), and the therapy algorithm may analyze of incoming data to determine whether or not the subject's current parameter set should be changed, and to generate the new parameters to be loaded onto the subject's implant 120. Therapy algorithms may be configured to update different therapy parameters according to different time scales, for example, determining and providing a stimulation amplitude update multiple times per hour, but only determining and providing and sampling parameter update every few weeks, and so on.

Thus, the configuration of parameters in step 401 may be determined by a neuromodulation therapy algorithm executing on a platform server 110. As discussed above, the set of neuromodulation therapy parameters may be transmitted securely from the platform server 110 via communication networks 140 to the subject's mobile device 130, which can then transmit the parameters to the subject's implant device 120 via a secure short-range radio connection. In other examples, the parameters in step 401 may be transmitted to the implant 120 directly from a clinician programmer device (e.g., during an in-clinic subject visit and/or using a wide-area network or the Internet).

In some embodiments, even though neuromodulation therapy algorithm may be used to update a subject's parameters, the initial parameter set within the subject's neuromodulation therapy implant 120 may be determined by a clinician. For example, the clinician may define the subject's initial neuromodulation therapy parameters, define one or more safety boundaries for the therapy (e.g., a maximum stimulation amplitude for each electrode contact). The clinician, based on consultation with the subject, may also prioritize treatment outcomes in terms of the subject's symptoms, side effects, and biomarkers. For instance, in a deep brain stimulation therapy for Parkinson's disease, the clinician may want to optimize with respect to tremors, rigidity, freezing of gait, dyskenisia, and minimizing side effects. For treatment of individual subjects with Parkinson's disease, the clinician and/or subject may prioritize these factors or may select a specific combination of these factors to be optimized (e.g., via a binary selection and/or by specifying a weight to be applied to each of one or more of the factors). Safety boundaries (e.g., as indicated by an initial programmer or clinician), clinical objectives (e.g., as specified by the clinician, and subject data (e.g., identifying age, symptom characterization, etc.) may be used to determine adjustments in the underlying stimulation parameters, to optimally achieve the desired clinical objectives without violating the defined safety boundaries. As described below in more detail, therapy algorithms may be based on any of several different types of search algorithms, which may execute effectively to identify the optimal therapy for the subject while avoiding getting stuck at local maximums. These therapy algorithms may rely on historical subject data to recognize patterns, speed up the programming process, and need not be reliant on discrete clinician judgment events.

In step 402, subject data may be received from one or more data sources. The subject data can include data that was collected during or after the neuromodulation therapy is administered to the user. Thus, the subject data collected in step 402 may be analyzed to determine the effects of the neuromodulation therapy using the parameter set configured into the implant 120 in step 401. As discussed below in FIGS. 5A-5D, the subject data may include various types of data from different data sources, including brain signal data, subject symptom data, biomarkers, and/or subject monitoring data from external devices (e.g., cameras, heartrate monitors, activity trackers, etc.).

In step 403, based on an analysis of the subject data received in step 402, a determination may be made as to whether to modify the subject's neuromodulation therapy. These determinations may be performed by comparing the subject data received in step 402 to previous data readings, safety ranges, and/or desired ranges of subject data (e.g., brain signal data, biomarker data, subject symptom data, etc.). In some instances, if the subject data analyzed in step 403 falls within the desired or expected ranges (403:No), then the therapy may continue without modification. However, if the analysis in step 403 determines that the subject's therapy is to be updated or modified (403:Yes), then the process may proceed to steps 404-405 to determine and implement the neuromodulation therapy modifications.

In step 404, one or more neuromodulation therapy modifications is determined, and in step 405 the determined modifications may be implemented via the implant device 120. As discussed below in FIGS. 5A-5D, the modifications may be determined for and implemented at various different levels in the distributed computing architecture 100. For example, any of the subject's implant device 120, subject's mobile device 130, platform server 110, and/or clinician or research systems 150-160 may perform steps 402-405. As discussed below, these various devices/systems may each perform separate continuous reprogramming processes based on different types of received subject data, and using different techniques for modifying the subject's neuromodulation therapy.

Figure 5A:
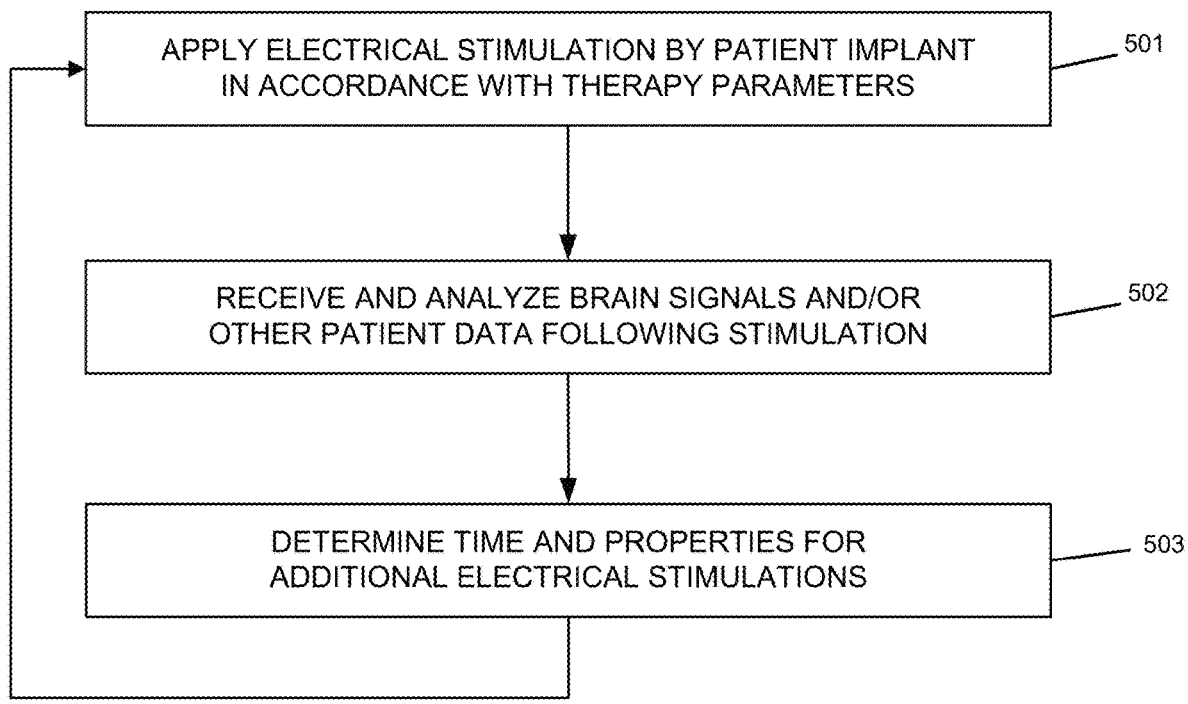
FIGS. 5A-5D are flowcharts of example processes for continuous monitoring and modification of neuromodulation therapies according to aspects of the present disclosure.
Figure 5B:
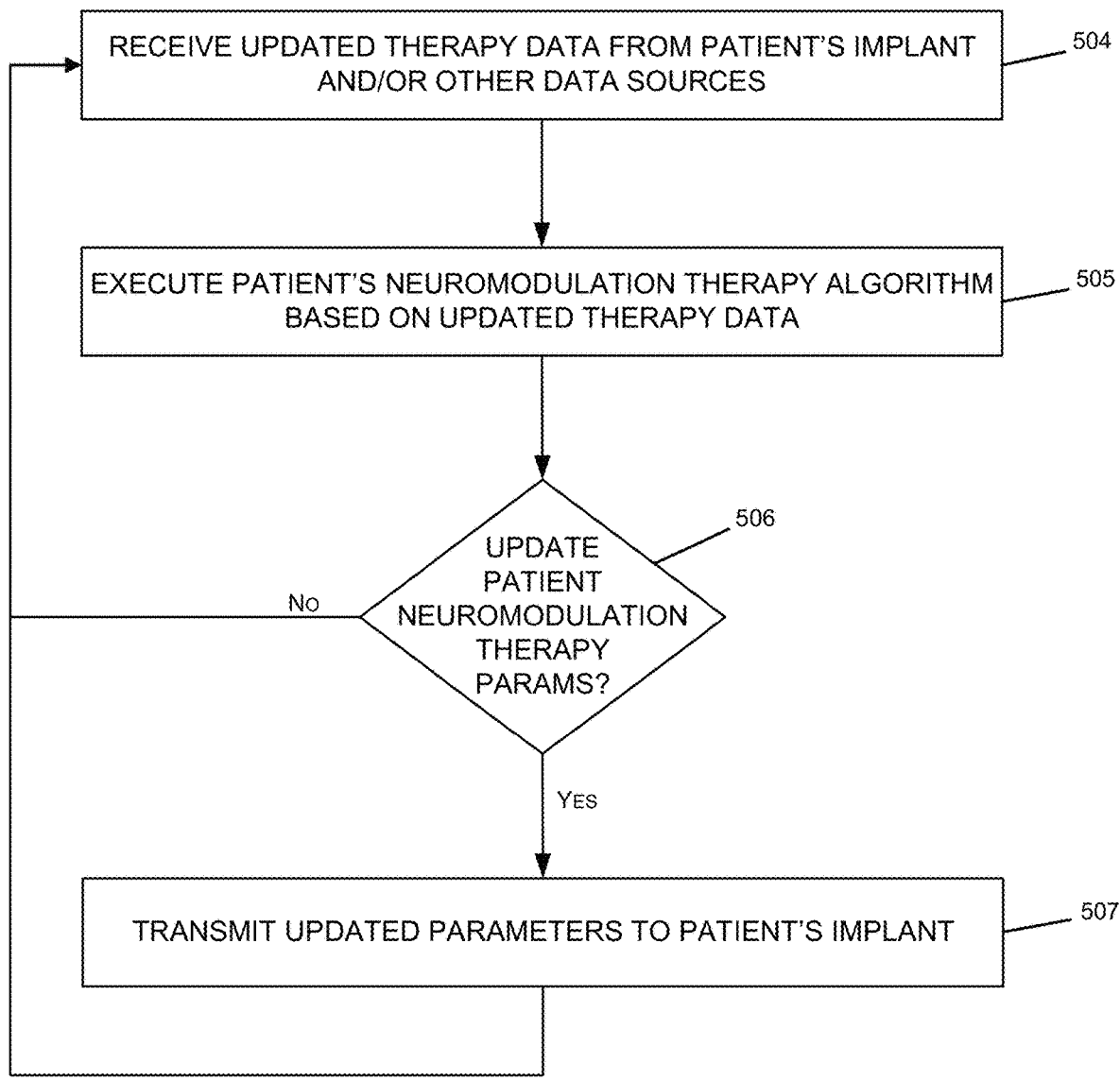
Figure 5C:
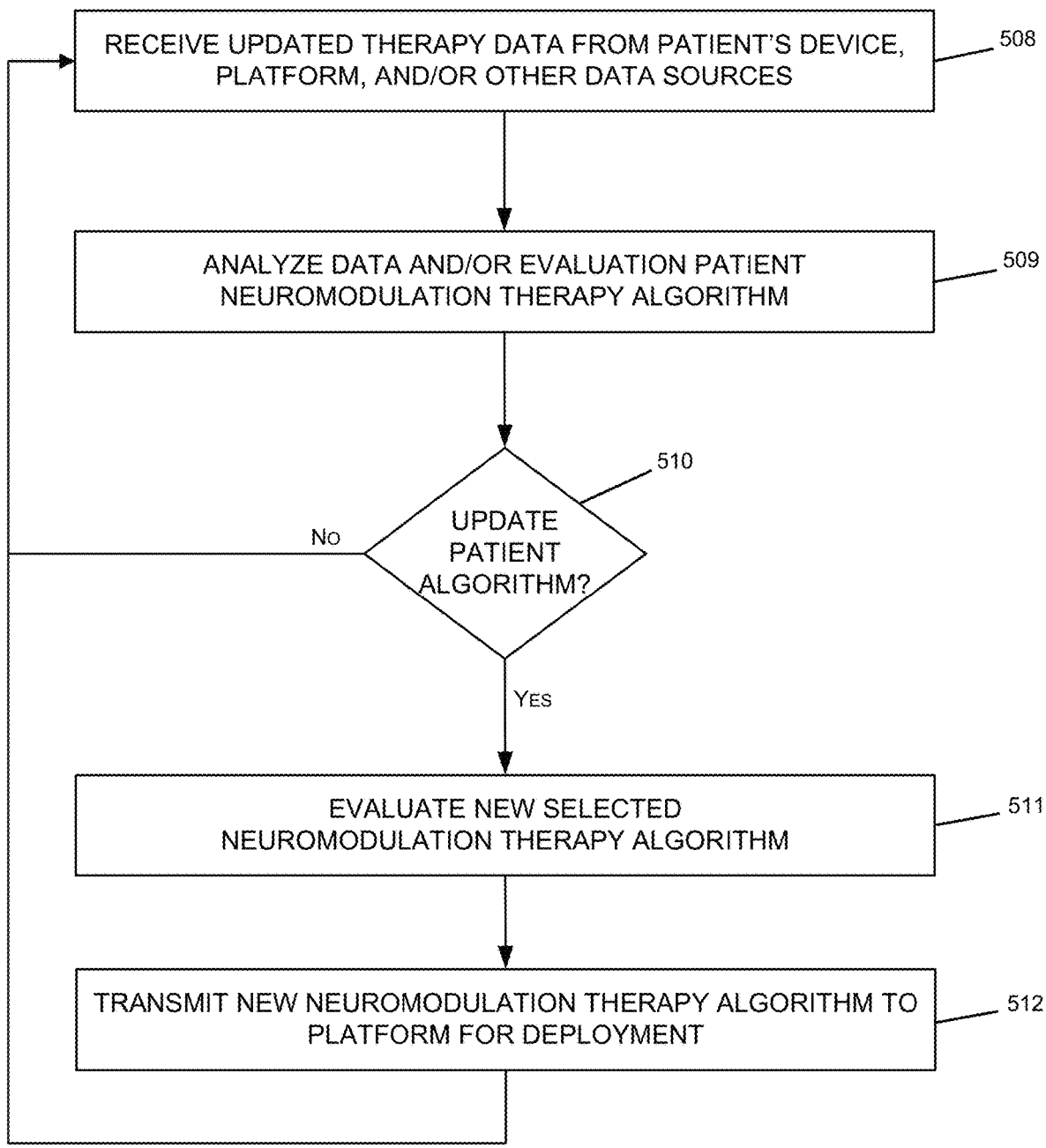

FIGS. 5A-5D are flowcharts showing four different examples of continuous monitoring and modification of neuromodulation therapies which may be performed at different levels within the distributed computing architecture 100. In FIG. 5A, a processing loop is described for determining electrical stimulations during neuromodulation therapy, which may be implemented entirely within an implant device 120. In FIG. 5B, another processing loop is described for updating a set of neuromodulation therapy parameters, which may be implemented within one or more platform servers 110 in communication with an implant device 120. In FIG. 5C, another processing loop is described for updating a neuromodulation therapy algorithm, which may be implemented within one or more research or clinician systems 150-160 in communication with platform servers 110. Finally, in FIG. 5D, process is described for updating a neuromodulation therapy algorithm in response to an overriding update to the neuromodulation therapy parameters. It should be understood that these techniques may be performed individually and/or any combination by the various components within the distributed computing architecture 100.

Referring now to FIG. 5A, a flowchart is shown illustrating a process for determining upcoming stimulations to be provided by a neuromodulation therapy implant device 120. The processing loop 501-503 may (but need not) be implemented entirely within an implant device 120, and may gain speed processing advantages from the local computation. In step 501, the implant 120 provides a stimulation, such as an electrical stimulation to the subject's brain or nervous system. The stimulation in step 501 may be made in accordance with a set of neuromodulation therapy parameters, and thus may be defined by a particular location (e.g., a cathode contact), a stimulation amplitude, and a stimulation frequency, etc. In step 502, the implant device 120 uses its onboard sensors (e.g., bioelectric sensors 344) and other sensors/data acquisition systems to receive and analyze subject data, such as voltage signals (e.g., intracellular recordings from an implanted part of the implant device or extracellular recordings from a non-implanted part of the implant device) from the brain, accelerometer signals from an inertial measurement unit (IMU), and/or other onboard sensors within the implant 120. In step 503, the implant 120 may determine one or more characteristics for subsequent electrical stimulations to be administered to the subject, based on the data detected in step 502. For example, the implant 120 may determine a location (e.g., select a cathode contact), amplitude, frequency, pulse width, etc., for a future electrical stimulation to be delivered by the implant 120. As noted above, the loop in FIG. 5A may operate entirely within the implant 120, which may be advantageous in certain cases when the speed and responsiveness of the change in therapy is critical. For example, the loop in FIG. 5A may be used to detect and respond to dyskinetic event in a Parkinson's subject, or a seizure event in a subject with epilepsy.

Referring now to FIG. 5B, another flowchart is shown illustrating a process for updating the neuromodulation therapy parameters within an implant device 120. Steps 504-507 of FIG. 5B may be performed by a neuromodulation therapy platform server 110 in conjunction with an implant device 120. For example, steps 504-506 may be performed during execution of a therapy algorithm which may be running continuously for a particular subject within the platform servers 110. The therapy algorithm may be configured to process continually or repeatedly receive and process data from the subject's implant device 120 and/or various other data sources providing subject data.

In step 504, the subject's neuromodulation therapy algorithm executing on the platform server 110 may receive updated data relating to the subject's ongoing neuromodulation therapy. The data received in step 504 may include data from the subject's implant device 120, such as brain signal data, biomarker data, etc. The set of therapy parameters that were used during a time period during which the updated therapy data was collected can also be received (e.g., from used by the implant 120). The data may be received either as a continuous data stream or as periodic transmissions, and it may arrive via a transmission path including the subject's mobile device 130, one or more network devices 220, communication networks 140, etc. Additional data may be received in step 504 for separate data sources, such as the subject's mobile devices 130 (e.g., smartphones, smart watches, sleep/activity trackers, etc.), and/or one or more of the external subject monitoring devices discussed above in relation to FIGS. 2A-2B. Such external monitoring data may relate to the subject's behaviors and activities, and may be relevant to detect certain symptoms and side-effects of therapy (e.g., tremors, gait smoothness, sleep patterns, etc.), as well to determine relevant context/environmental factors at the subject's location, temperature/weather factors, lighting and noise factors, etc. In some cases, the data received in step 504 also may include user feedback provided manually by the subject, for example, in the form of an electronic survey provided on the subject's smartphone 130, in which the subject may respond to questions about his/her recent symptoms, side-effects, mood, activities, etc.

In step 505, the subject's neuromodulation therapy algorithm may be executed on the platform servers 110, to determine an updated set of neuromodulation therapy parameters for the subject. In some embodiments, the subject's neuromodulation therapy algorithm may be running continuously within the platform servers 110, while in other embodiments the subject's neuromodulation therapy algorithm might not initially be running, but may be initiated in response to receiving the updated data in step 504. As discussed above, the therapy algorithm executed in step 505 may be subject-specific, and may include various algorithm types configured to monitor the subject data, enforce the subject's safety boundaries, and improve/optimize for the subject's desired clinical objectives. Examples of several possible neuromodulation therapy algorithm types that may be used are described below. The output of these algorithms may include modified neuromodulation therapy parameters. A modified neuromodulation therapy parameter can include a new neuromodulation therapy parameter (e.g., that is to replace a previously used neuromodulation therapy parameter) or a delta that indicates how a previously used neuromodulation parameter is to be changed. It should be understood that different parameters may be adjusted according to different time scales. That is, the therapy algorithm executed in step 505 may output modifications to different parameters at different times, by (for example) more quickly or more frequently outputting a first parameter linked to very fast biomarker (e.g., measured in instantaneous brain or motion signals), while less quickly or less frequently outputting other parameters linked to slower biomarker (e.g., brain signals averaged over time, reported subject mood, symptoms, or medications, etc.). Similarly, some therapy parameters may be weighted more heavily based on their effect on the subject (MSBs for stimulation amplitude, electrode contact bits, etc.), while other less important parameters may be weighted less.

Examples of Neuromodulation Therapy Algorithms

Stochastic Gradient Descent (SGD) algorithms may be executed to iteratively explore an n-dimensional space (e.g., deep brain stimulation system configuration parameters) to optimize the function $F(x)$ which may include an output variable that represents the overall subject state. An SGD algorithm may provide the basis for selecting adjustments to therapy parameters or new therapy parameters. The adjustment or new parameters may be predicted to result in an improved overall subject state compared to a subject state associated with the previously used therapy.

Ensemble Machine Learning. In some embodiments, data complexities (e.g., arising from availability of multiple types of data, data from multiple sources, sub-optimal data confidence, etc.) may limit the extent to which any single machine-learning algorithm can accurately predict data outputs. However, by stacking two or more models, an ensemble machine-learning algorithm may be used to create a more accurate subject therapy optimization algorithm. For example, as the subject's therapy parameters are adjusted at each cycle of the loop in FIG. 5B, a machine-learning model may be trained on the previous inputs and their known outputs (e.g., resulting subject biomarkers). The trained model then may be used to predict the subject state for various possible adjustments, all of which may be used as inputs to an SGD algorithm to search for the optimal subject parameters to try as the next iteration of the processing loop in FIG. 5B. This way, the SGD algorithm may explore the entire optimization gradient, rather than only relying on the few actual configurations applied so far to this subject as samples. As each subsequent adjustment is applied to the subject in FIG. 5B, the recorded outcome may be used as feedback to improve the model of the (e.g., including an ability to simulate the subject's reactions); and therefore may improve the probability that the next adjustment will move toward the optimal set of therapy parameters for the subject. Additionally, in some embodiments, a third clustering model may be stacked to the algorithm to allow bootstrapping of the therapy algorithm, so that the platform server 110 need not guess for first few parameter configurations to try on a new subject. By taking anonymized training data collected from previous subjects, the new subject may be classified based on either known health factors and/or initial biomarker feedback from the subject, into a known cluster (or group) of subjects having similar physiological profiles. The algorithm then may use the parameters determined to be optimal for that cluster of subjects as an initial parameter configuration, and then attempt to further optimize for the individual subject in an iterative fashion as described earlier.

Hidden Markov Model (HMM). Every subject may have a number of natural biological variations that may be unknown or unquantified to the clinician. In these instances performing iterative adjustments of parameters and effect monitoring can be used to uncover the obscured underlying data and/or to identify effective therapy parameters. An HMM may be used as an effective middle layer for the ensemble machine-learning model discussed above, to discover the subject's latent variables that explain their reactions to different stimuli, thus providing more accurate predictions than are possible with a simpler linear regression model.

Feature Decomposition. For any of the models described above, correlation heatmaps may be built quickly within the platform server 110 as sample points are recorded. This allows the algorithm to quickly discover and/or convey which therapy parameters have the most and least effect on various subject biomarkers, other subject data, and the subject's overall state. This data then may be used to weight or prune individual features in the algorithm's input, thereby reducing the high vector dimensionality which may be a bottleneck to solving the optimization problem in a timely and performant manner.

In step 506, the platform server 110 may determine, based on the execution of the subject's neuromodulation therapy algorithm in step 505, whether or not to update the therapy parameters in the subject's implant 120. For example, if the models/algorithm(s) executed in the most recent iteration of step 505 indicate that the subject is at or near (e.g., within a predefined absolute or relative amount from) an optimal overall subject state, then platform server 110 may determine not to update the subject's neuromodulation therapy parameters (506:No). Even if the current subject data indicates that the subject is not at an optimal state, and that the subject's overall state could likely be improved by updating the therapy parameters, the platform server 110 still might not to update the subject's neuromodulation therapy parameters (506:No) based on one more other factors, including configuration settings or preferences that limit the frequency of therapy parameter updates; or prohibit therapy parameter updates at certain times or while the subject is engaged in certain activities (e.g., driving, exercising, etc.). However, in other cases, if the algorithm determines in step 505 that the subject is not at an optimal overall state, and that the subject's state could likely be improved by updating the therapy parameters, the platform server 110 may decide to update the subject's therapy parameters (506:Yes), using the recommended updated parameter set provided by the most recent execution of the models/algorithms in step 505.

In step 507, the platform server 110 may transmit the subject's updated set of neuromodulation therapy parameters to the implant device 120. As discussed above, such transmissions may occur via a secure transmission path including the one or more communication networks 140, one or more network devices 220, and the subject's mobile device 130 or other subject device (e.g., a specialized neuromodulation therapy remote control), which is configured to wirelessly and securely transmit the updated therapy parameters to the subject's implant device 120.

In some embodiments, the transmission and/or deployment of updated neuromodulation therapy parameters to a subject's implant 120 may include or trigger notifying and/or receiving consent or confirmation from one or more users, such as the subject or the subject's clinician. For example, if the platform server 110 determines that the subject's therapy parameters should be updated (506:Yes), then in some cases the platform server 110 may transmit a notification to one or more subject devices 130 (e.g., via email to the subject's email address, via app-based alert to the subject's smartphone or smart watch, etc.), and/or to one or more clinician systems 160. In some embodiments, the subject, the clinician, or both may be required to review and consent to the proposed updates to the subject's therapy parameters. Such consent requirements may be enforced at the platform server 110 and or at the subject's mobile device 130 responsible for transmitting the updated parameters to the implant 120.

Additionally, during the execution of the subject's neuromodulation therapy algorithm in step 505, certain data or events may trigger notifications to the system 160 of the subject's clinician. For example, certain specific subject data (e.g., particular biomarker configurations), certain specific recommendations for parameter changes, and/or system events such as timeouts, may trigger such notifications. These triggered notifications may allow the clinician to adjust broader parameter sets stored for the subject inside the platform server 110, such as safety ranges or changes to the overall therapy algorithm itself.

Referring now to FIG. 5C, another flowchart is shown illustrating a process for updating the neuromodulation therapy algorithm that is executed within the platform servers 110 for a particular subject. Steps 508-512 of FIG. 5C may be performed by a research system 150 or a clinician system 160, in conjunction with the platform servers 110 and/or historical subject data repositories 170. Thus, the processing loop FIG. 5C corresponds to the updating of the therapy algorithm itself (e.g., the algorithm that executes to determine updates to the therapy parameters). In some embodiments, this processing loop may be executed less often than the processing loops shown in FIGS. 5A and 5B, and/or may generally operate further from the implant device 120 in the distributed architecture. As described below, using process steps 508-512, researchers and clinicians may access the platform server 110 via APIs 116, to view subject data across individual and population levels, and to make higher-level decisions regarding the appropriate or optimal therapy algorithm to be used for a particular subject. As a subject's needs and overall state may evolve over time, new therapy algorithms may be selected (and/or designed) for the subject. As described below in more detail, clinicians and/or researchers may use certain features of the platform servers 110 to design, build, test, and implement new neuromodulation therapy algorithms for individual subjects. Historical subject data from previous therapy algorithms also may be retrieved from data repositories and used to predict the stability, power consumption, and even efficacy of new therapy algorithms.

The process in FIG. 5C may execute on the platform servers 110, and/or on an external system such as a researcher system 150 or clinician system 160. In some cases, a processing loop 508-512 may run continuously, either on the platform servers 110 or an external system 150/160, in order to continuously receive and analyze data in order to determine whether or not the subject's current neuromodulation therapy should be updated. In other cases, the process 508-512 might not loop continuously, but may be executed as a discreet process 508-512, for example, in response to a request received via a researcher system 150 or clinician system 150 to review and evaluate the subject's current neuromodulation therapy algorithm.

In step 508, the process may receive (or retrieve) neuromodulation therapy data relating to a particular subject. The data received (or retrieved) in step 508 may include any of the data received in step 504 in the process for updating therapy parameters, as well as data from additional data sources. For instance, the platform server 110, or the researcher or clinician system 150-160, may access one or more neuromodulation therapy data repositories 170 to retrieve historical data relating to neuromodulation therapy previously administered to this subject and other subjects. Such historical data may include a chronological record of subject data, including the previous therapy algorithms that were executed for that subject during various time periods, the resulting changes in therapy parameters performed for the subject, and the subsequent subject data from the time periods following any changes in a subject's therapy algorithm or parameters.

In step 509, the various neuromodulation therapy data received (or retrieved) in step 508, relating both the particular subject and/or previous data for other subjects, may be analyzed and the subject's current therapy algorithm may be evaluated. Then, in step 510, the process may determine whether or not to update the subject's neuromodulation therapy algorithm based on the analysis and evaluation in step 509. Steps 509 and 510 may performed manually in some cases, by a researcher or clinician during a clinical review/evaluation the subject's current neuromodulation therapy. In other cases, steps 509 and/or 510 may be performed via automated processes within the platform server 110 or the researcher or clinician systems 150-160. For example, steps 509 and/or 510 may include the execution of machine-learning models trained based on historical subject data including the subject's algorithm, algorithm changes, and the subsequent performance of the algorithm (e.g., for stability, frequency of parameter changes, etc.) and the response of the subject (e.g., resulting overall subject state, etc.). Thus, the data analysis and algorithm evaluation processes in step 509-510 may use similar or the same algorithms and/or modeling techniques described above in steps 505-506 for analyzing and evaluating the subject's therapy parameters.

In step 511, if the process has determined that the subject's neuromodulation therapy algorithm should be updated (510:Yes), the recommended optimal algorithm determined in steps 509-510 may be evaluated by the clinician/researcher systems 150/160 and/or the platform server 110, to confirm that the selected algorithm is suitable and appropriate to be used as the subject's new neuromodulation therapy algorithm. For example, one or more of the various different neuromodulation therapy algorithms described herein, and/or other algorithms, may be executed to analyze the subject's current therapy. If the one or more algorithms determine that the current subject therapy is "suboptimal," based on a predetermined threshold, then the algorithms may determine that a new therapy algorithms is to be selected for the subject. The threshold for determining whether or not the subject's current therapy is suboptimal may be set manually (e.g., by the clinician and/or subject) or programmatically, for example, based on input from the clinician and/or subject defining an optimal weighting of providing effective therapy versus controlling negative side effects.

Step 511 also may include various automated steps, and/or a manual review process to be performed by the subject, clinician, or researcher. For example, automated simulation routines may be executed in step 511 during which the selected algorithm is executed based on current subject data and/or historical subject data from similar subject groups, and the execution of the algorithm may be evaluated by the simulation routine with respect to the predicted efficacy of the subject's neuromodulation therapy with the new algorithm, the predicted stability of the new algorithm, the predicted power consumption rate of the subject's implant 120 under the new algorithm, and so on. Manual evaluation processes in step 511 may include transmitted notifications to the subject (via the subject's mobile device 130) and/or clinician (via the clinician system 150) to inform and/or request approval for the proposed algorithm change.

In step 512, the new neuromodulation therapy algorithm selected for the subject may be transmitted to and deployed on within the platform servers 110, in a manner to overwrite or replace the subject's current therapy algorithm. In some embodiments, step 512 may require additional steps including compiling and building the selected therapy algorithm, pre-configuring the algorithm variables and settings, and deploying the executable algorithm within a platform server 110 (e.g., a secure cloud service platform).

Figure 5D:
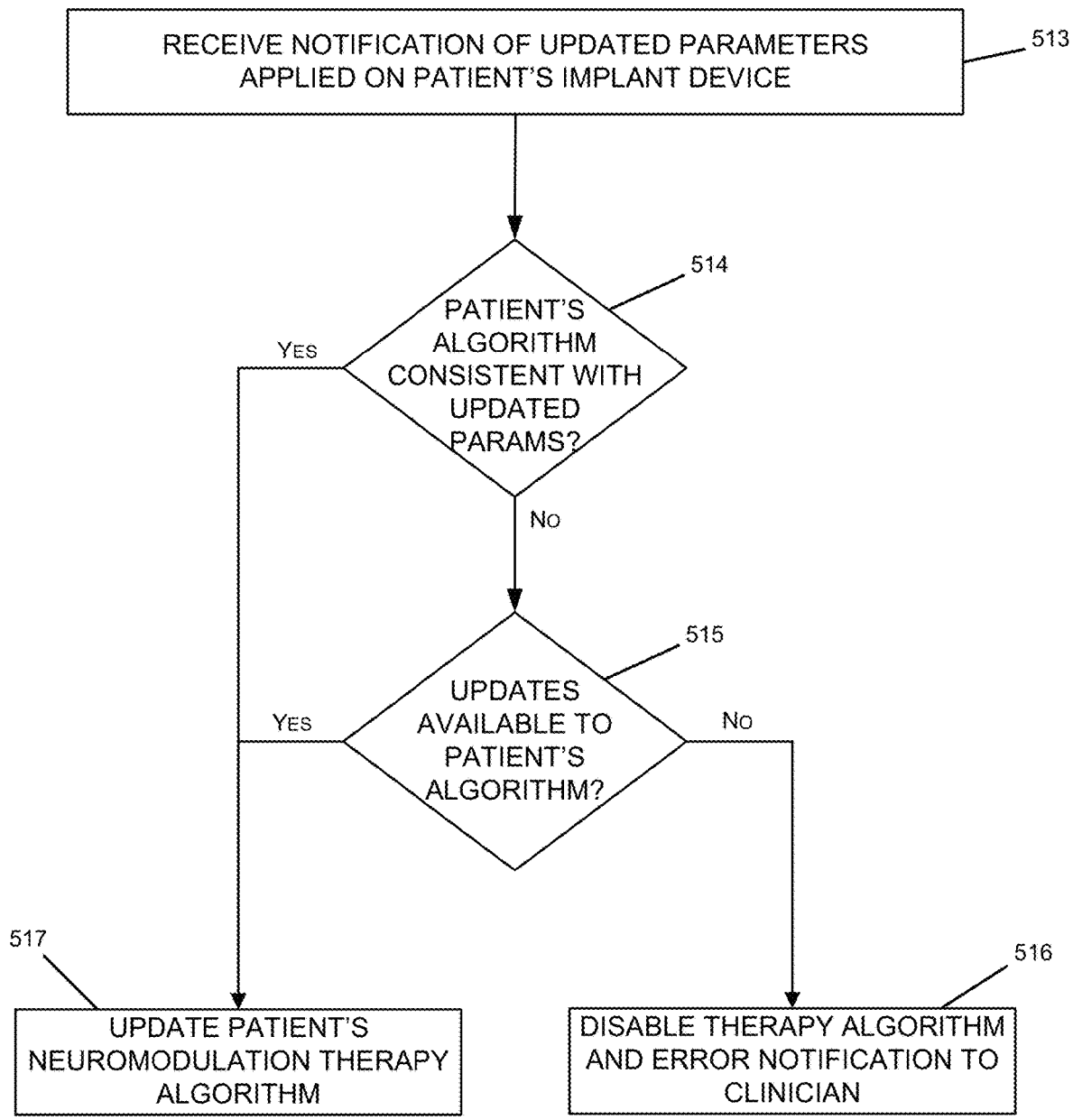

Referring now to FIG. 5D, another flowchart is shown illustrating a process for updating a neuromodulation therapy algorithm in response to an overriding update to the neuromodulation therapy parameters. This process relates to instances when a user (e.g., a subject or a clinician) has been received that corresponds to a request to expressly override the output of the subject's therapy algorithm executed by the platform servers 110, and to update the therapy parameters to the implant directly. For example, in some embodiments, a neuromodulation therapy subject may be provided with a subject remote control, which may be a controller device allowing the subject to independently adjust their therapy parameters, without informing or receiving authorization from the platform server 110 and/or clinician. A subject remote control for neuromodulation therapy may be a limited-featured controller which supports only limited ranges of parameter adjustments, and along limited degrees of freedom (e.g., a predetermined range of voltage amplitude). In some cases, the subject's smartphone 130 or other mobile devices may support similar functionality to enable the subject to adjust their own therapy parameters within limited ranges and degrees of freedom. Additionally, in some embodiments, a clinician programmer device may be a full-feature device with a graphical user interface supporting clinician control over all or most of the implant features and degrees of freedom. Although these devices are shown in the distributed computing environment 100, they may be used in certain embodiments to support hybrid systems with the platform server 110, providing some control to subject and/or clinician with respect to decision making, which may be desirable in some cases to reduce subject risk.

In step 513, the platform server 110 may receive a notification that a subject's neuromodulation therapy parameters have been updated independently (i.e., not based on the execution of the therapy algorithm). For instance, in a hybrid system as described above, the subject may independently modify their therapy parameters using a subject remote control (or other personal computing device 130), or the clinician may update the subject's therapy parameters using a clinician programmer device. The notification in step 513 may be transmitted by the updating device (e.g., subject remote control, clinician programmer device, etc.), or if those devices are non-networks or not configured to communicate with the platform servers 110, the notification may correspond to a synchronization process between the implant 120 and the platform server, via the subject's mobile device 130.

In step 514, the platform server 110 may analyze the subject's updated therapy parameters and determine whether or not the subject's current therapy algorithm is compatible with the updated therapy parameters. For example, if a subject/clinician manually updates the subject's therapy parameters, the platform server 110 may determine if the manually updated parameter values correspond to the parameter settings predicted by the subject's therapy algorithm. If they do not correspond (i.e., are not compatible) (514:No), the platform server 110 then may attempt to update the subject's current therapy algorithm to a new therapy algorithm (e.g., a recalibration step). To recalibrate the algorithm, the platform server 110 may adjust different weighting parameters or other calibration parameters in the algorithm, so that the optimum output of the algorithm agrees with the selected output as defined by the clinician and/or subject. If this is also not possible (515:No), then the platform server 110 in step 516 may allow the implant 120 to keep the independently updated therapy parameters, but may disable the current therapy algorithm and provide an error notification to the clinician system 160 to inform the clinician a new therapy algorithm is needed. Otherwise, if either the independently updated therapy parameters are compatible with the current therapy algorithm (514:Yes), or if the subject's therapy algorithm can be updated (515:Yes), then necessary updates/recalibrations (if any) are made to the subject's therapy algorithm in step 517.

II. Neuromodulation Therapy Development Environment

Additional aspects of the present disclosure relate to therapy development environment (TDE) that includes GUI-based software tool/platform for designing and developing neuromodulation therapy algorithms. In some embodiments, the TDE may include compilers, APIs, hardware model data and software libraries, and a therapy simulator to allow even non-technical users to design, develop, test, and deploy subject-specific neuromodulation therapy plans/algorithms. The TDE, described below in detail, may provide a layer of abstraction between the executable code running on the platform servers 110 (e.g., on the cloud) and in the implant device 120, and the subject's neuromodulation therapy as described by a clinician or other software-technical personnel, using a high-level programming language (e.g., Matlab or Python), or even a limited pseudocode version of these languages.

In some embodiments, the TDE may be a simple and non-GUI therapy development interface, having an API-like configuration to support therapy developer interaction with the platform servers 110. Additionally or alternatively, the TDE may be implemented as complex system of custom integrated development tools for a therapy developer, enabling efficient development of new therapy algorithms based on some high-level descriptive language from the user. One or more compilers and/or constructors may be included in the TDE (or implemented separately in conjunction with the TDE), which are configured to translate the high-level description of the therapy as provided by the therapy developer into executable code outputs to be run on the platform servers 110 and/or on the subject's implant device 120. In some embodiments, compilers/constructors may optimize for power consumption the specific hardware configuration selected within the TDE, for example, by minimizing requirements for power-consuming communication between the implant device 120 and the subject's mobile device 130.

Figure 6:
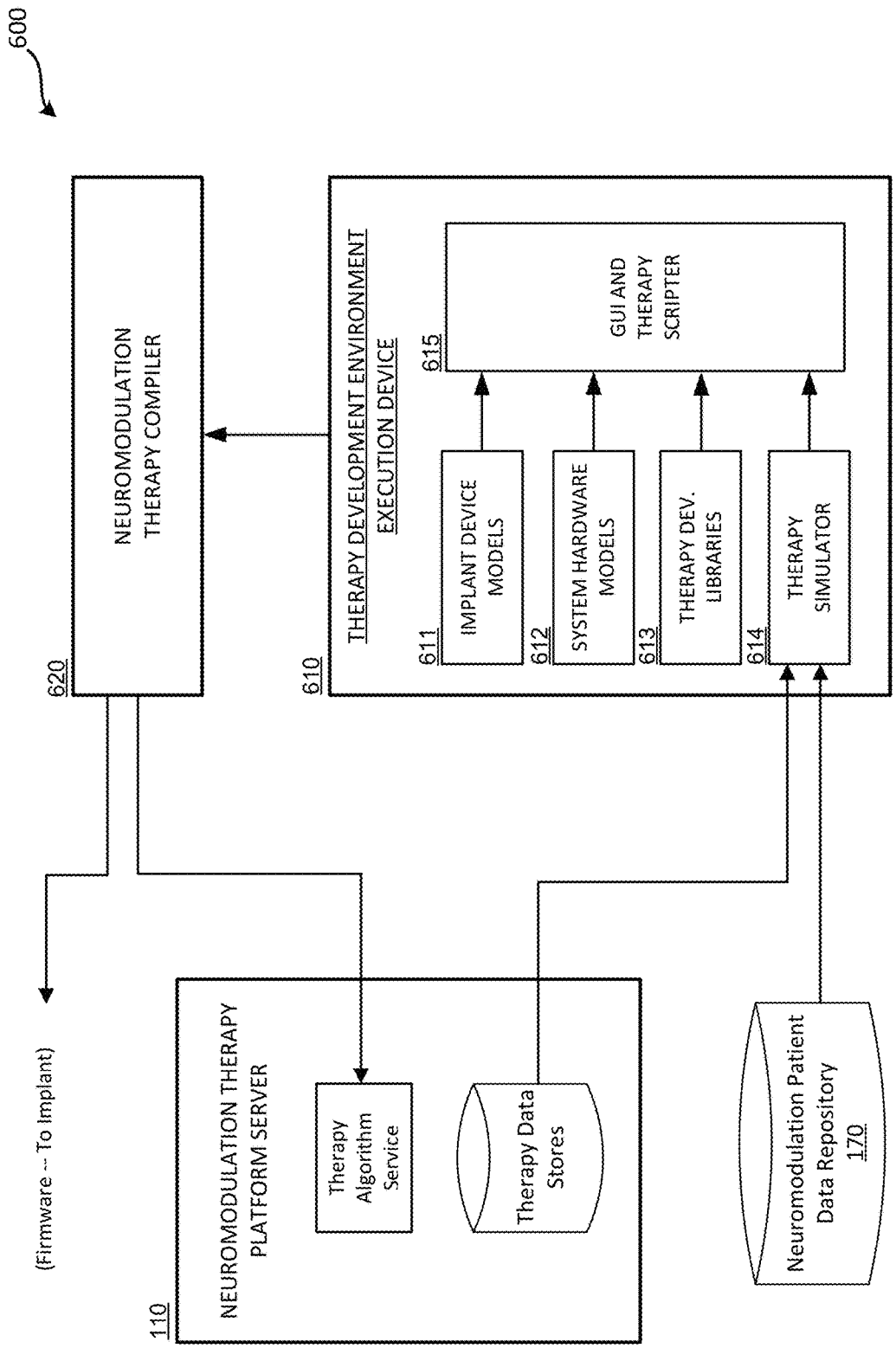
FIG. 6 is a block diagram of a neuromodulation computing environment according to aspects of the present disclosure.

Referring now to FIG. 6, another example computing environment 600 is shown, including a therapy development environment (TDE) execution device 610, compiler 620, and platform server 110. In some embodiments, computing environment 600 may correspond to same distributed computing environment 100 discussed above. As shown in this example, the TDE execution device 610 may be implemented separately from the platform servers 110 (e.g., in a cloud-based therapy platform); however, in other examples, the TDE execution device 610 and/or the therapy compiler 620 may be implemented within one or more platform servers 110 (for either cloud-based or non-cloud architectures). The TDE execution device 610 may provide a GUI-based design and development interface, to allow neuromodulation therapy designers (e.g., clinicians, researchers, subjects, etc.), to design, build, and test neuromodulation therapy algorithms. As shown in FIG. 6, in some embodiments the TDE execution device 610 may refer to a client computing device that receives and executes software to generate a TDE on the client device, and receive data collected via the user interface 615 of the TDE. However, in other examples, the TDE execution device 610 may refer to a server that generates and transmits the TDE to a separate client device which displays the TDE interface 615.

The TDE execution device 610 may include shown one or more data stores (e.g., local databases, spreadsheets, specifications files, etc.) storing the specifications and properties for a number of implant devices models 611, specifications and properties for a number of other system hardware devices 612 (e.g., the subject's smartphone 130 and other personal computing devices, various additional sensors or subject monitoring devices, and/or the platform servers 110 and data repository servers 170), and the specifications and properties from one or therapy development libraries 613 (e.g., a library of the various code and functions that a therapy developer may choose to include in a therapy algorithm design). For example, during interactions with the TDE, a user may have options to select from various basic signals processing functions, such as Fourier transforms, coherence, windowed averages, thresholds, filters, etc. Users also may have options via the TDE to select any of examples of neuromodulation therapy algorithms described herein. Additionally, the TDE execution device 610 in this example includes a therapy simulator 614, described in more detail below, which may allow therapy developers to predict aspects of therapy performance for designs created within the TDE execution device 610, using historical subject data retrieved from the neuromodulation subject data repository 170. A GUI and therapy scripter component 615 may provide an interactive graphical user interface to allow the therapy developer to select combinations of neuromodulation therapy hardware components and/or neuromodulation therapy software, for designing and developing new therapy algorithms for deployment within a particular distributed architecture 100.

As shown in FIG. 6, after a therapy algorithm has been designed via the GUI and therapy scripter 615, the high-level code of the algorithm design may be compiled by the therapy compiler 620. In some embodiments, the compiler 620 may include one or more code analyzer modules to break down the received high-level code into a three separate components. An implant component may include the executable software (e.g., firmware) to be run on the implant device 120 itself. The implant component may be configured with certain execution settings, for example, timing for generating stimulation waveforms, on-chip thresholds, Linear Discriminant Analysis (LDA), or other compute parameters, etc. A network component may include software and configuration settings for handling communications between the implant 120 and the platform server 110, including settings for the frequency of communication (e.g., the frequency updates sent to and/or from the implant 120), and content. The network component may have a significant effect on power consumption, and thus the compiler 620 may be configured to minimize power consumption based on the implant-platform communications. Finally, a platform component may include the executable software configured to execute in the platform servers 110. In some cases, the compiler may build a platform component software expressly designed for execution within cloud-based platform servers 110. In some cases, the platform component built by the compiler 620 may be referred to as the therapy algorithm service (or therapy algorithm), and like the examples of therapy algorithms discussed above, may be configured to compute new subject-specific therapy parameters based on incoming subject biomarker data and/or other subject data received from various source.

Figure 7:
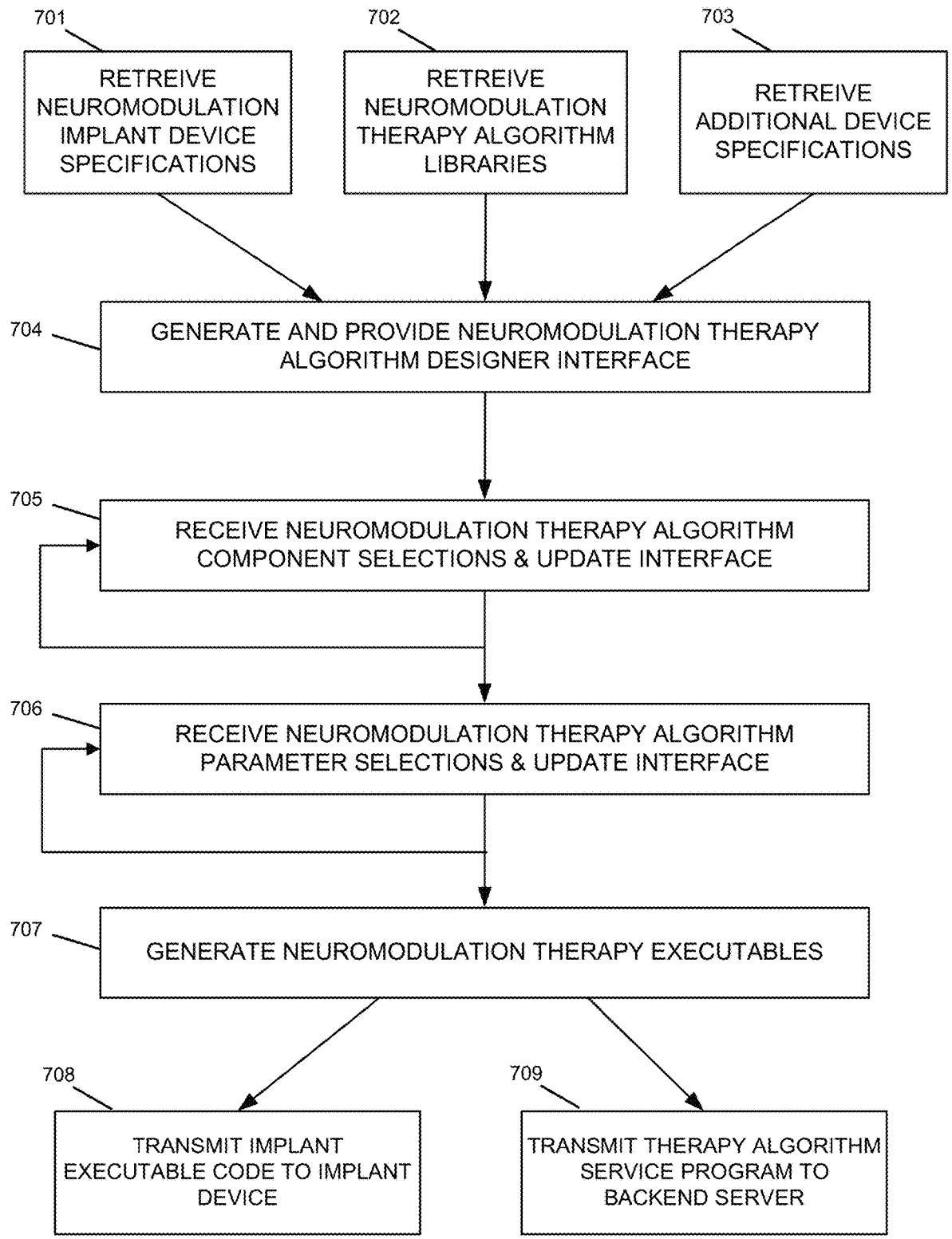
FIG. 7 is a flowchart of an example process for providing a neuromodulation therapy development environment according to aspects of the present disclosure.

Referring now to FIG. 7, a flowchart is shown illustrating a process for providing a neuromodulation therapy development environment (TDE) used to design and build neuromodulation therapy algorithm executables. The steps in this process may be performed by the TDE execution device 610, in conjunction with a therapy compiler 620, within a neuromodulation distributed computing environment 600. As noted above, the TDE execution device 610 may refer to a server or a client device in various embodiments.

In step 701-703, the TDE execution device 610 may retrieve various types of hardware/software specifications that may be used by the TDE execution device 610 to determine component compatibility and design optimization during the interactive therapy algorithm design process. In step 701, the TDE execution device 610 may retrieve device specifications/properties for a number of different models or types of neuromodulation therapy implant devices 120. Examples of specifications/properties that may be retrieved (or determined) and stored for implant devices 120 may include: whether or not the implant is an open loop or closed loop system, the variables defining the different types of the electrical stimulation that can be delivered by the implant (e.g., number and positioning of electrodes, min and max stimulation amplitudes, min and max stimulation frequencies, supported pulse widths and duty cycles, etc. Additional specifications/properties data received in step 701 for the implant devices 120 may include the numbers and types of bioelectric sensors, other subject biomarker monitoring capabilities, sampling rates for the implant's sensors, filter parameters for data acquisition systems, telemetry timing data, etc.

In step 702, the TDE execution device 610 may retrieve software specifications/properties for a number of software components that may potentially be executed by any of the computing devices within a neuromodulation distributed computing environment 100. For example, the TDE execution device 610 may retrieve and/or maintain a library of predefined software components capable of use within a neuromodulation distributed computing environment 100, including code functions to be executed by the firmware of the implant device 120, therapy algorithms and other routines to be executed by the (e.g., cloud-based) platform servers 110, additional software routines/functions to be executed on the subject's mobile device 130, etc. Examples of software components that may be user-selectable via the TDE user interface 615 may include a component to extract beta-signals from the implant, or a component block to extract sleep/wake cycles from brain signals, etc. In other examples, any stable software transform configured to received implant data as an input may be implemented via the TDE user interface 615.

In step 703, the TDE execution device 610 may retrieve additional device specifications/properties for the various other computing devices (e.g., non-implant devices) that may operate within a neuromodulation distributed computing environment 100. For example, device specifications and properties may be retrieved for multiple smartphone models and other subject computing devices. Devices specifications and properties may be retrieved also may be retrieved for any of the subject monitoring devices described in FIGS. 2A and 2B, or any other computing device/server that may operate within a neuromodulation distributed computing environment 100. The specifications and properties data for these additional devices may include data defining the features and functionality of the devices, device compatibility data, support communication types and protocols, native OS and other device software, etc.

In step 704, in response to a user initiation of the TDE, the TDE execution device 610 may generate and display an interactive graphical user interface 615 for the TDE, including representations of and/or options for selecting components corresponding to any of the various implant devices 120, additional computing devices, and software algorithms/components for which specification data was received in step 702. For example, referring briefly to FIG. 8, an example graphical interface display screen 800 is shown, including a workspace 810 for designing therapy algorithms, three drag-and-drop menus 820-840 containing selectable components corresponding to implant devices (820), therapy algorithms (830), and sensor devices (840). As shown in this example, the user may design, customize, and configure a therapy algorithms via the user interface 800, by selecting, parameterizing, positioning, and linking the selected components within the workspace 810.

Figure 8:
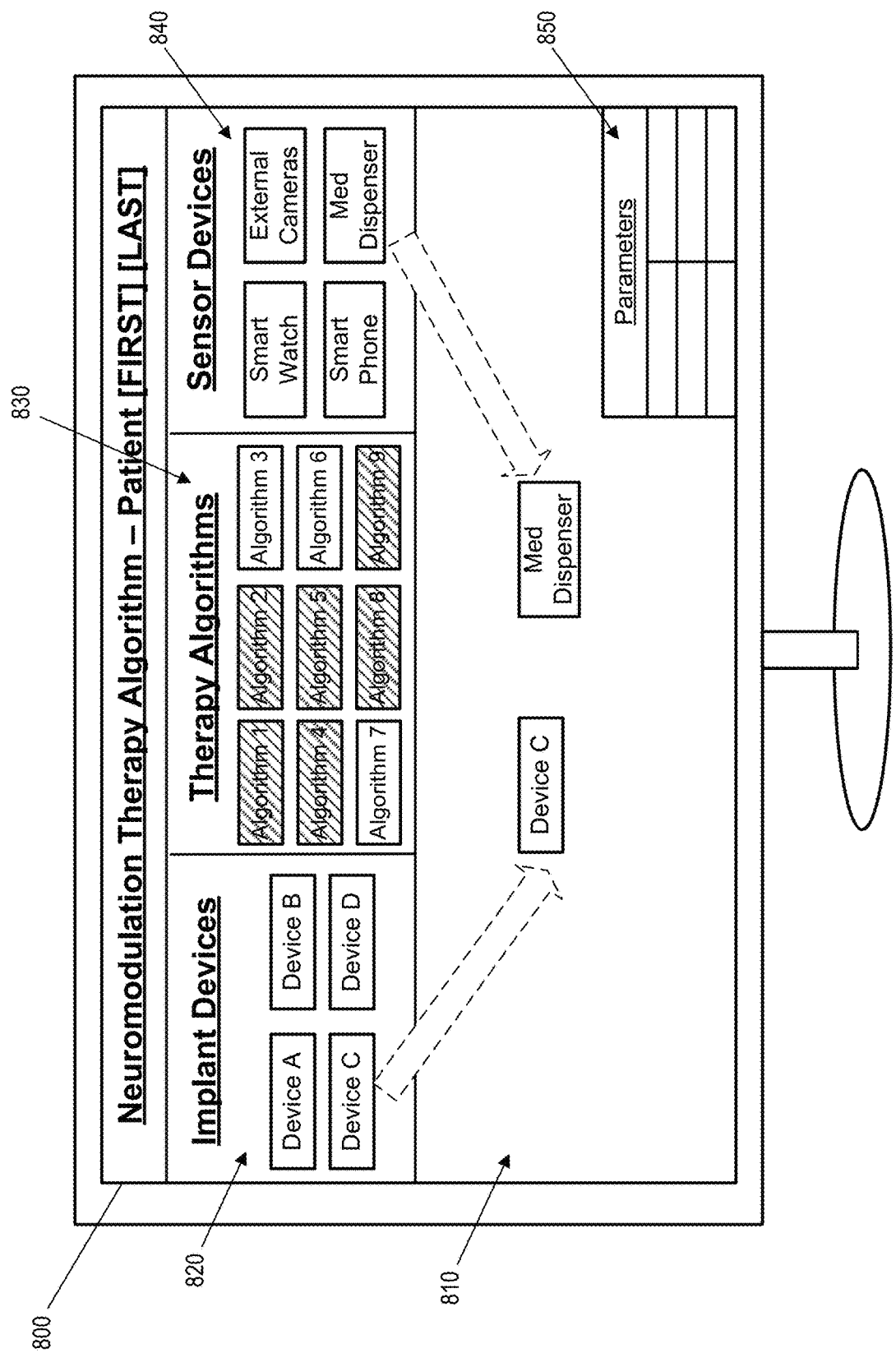
FIG. 8 illustrates an example graphical user interface for providing neuromodulation therapy algorithms according to aspects of the present disclosure.

In step (and loop) 705, the TDE execution device 610 may receive and process identifications of one or more interactions with the user, such as user selections of particular components. As shown in the example of FIG. 8, the user interface 800 may be automatically updated in response to the selection of a particular hardware or software component, by deactivating any other hardware or software components that are not compatible with the selected component. For example, if the user selects a certain hardware configuration for the implant device 820 and other available hardware devices 840, then the TDE execution device 610 may automatically restrict (e.g., via greying out, deactivating, syntax highlighting, etc.) the selection of certain incompatible therapy algorithm and/or other incompatible code and functions. For example, as shown in FIG. 8, the user has selected a particular implant device model ("Device C") and one particular sensor device model ("Med Dispenser"), and in response the TDE execution device 610 has deactivated several of the possible therapy algorithms, indicating that those deactivated algorithms are not compatible with the selected implant and/or sensor and thus are not available for selection via the user interface. Alternatively, if the therapy developer initially chooses one or more of the therapy algorithms 830 and/or other software code or functions, then in response the TDE execution device 610 may deactivate and prevent selection of any incompatible implants devices 820 and/or incompatible sensors or other hardware devices 840. The incompatibilities determined by the TDE execution device 610 in step 705 may represent, for example, two or more hardware components that are incapable of direct communication with one other, a selected therapy algorithm that may require data not collected by one or more of the implant devices 120 and/or other sensor devices, or a selected therapy algorithm that requires certain biomarker data and/or other subject data that must be retrieved by specialized sensors within the implant and/or other devices.

In step (and loop) 706, the TDE execution device 610 may receive and process therapy algorithm parameter selections via parameter window 850, including updating the user interface window 810 to activate/deactivate various selectable components based on determinations that those components are or are not compatible with the parameter selections of the user. In some cases, certain therapy parameters may be determined to be suboptimal (or even impossible) based on the selected configuration of hardware components, and thus those therapy parameters may be deactivated within the user interface 810. Similarly, certain hardware components may be determined to be suboptimal (or even impossible) based on the selected configuration of therapy algorithm and/or parameters, and thus those hardware components may be deactivated within the user interface 810.

In step 707, the TDE execution device 610 may compile the high-level code generated during the interactive therapy algorithm design process. The compiling can result in production of one or more neuromodulation therapy executables that are capable of running within the distributed architecture 100. In this example, the high-level therapy algorithm design code generated by the TDE execution device 610 may be passed off to a therapy compiler 620 configured to compile the code into multiple executable components. The executable components generated in step 707 may include an implant component containing the firmware to be run on the implant device 120, and a platform component containing the therapy algorithm service software configured to execute in the platform servers 110.

In step 708, the executables generated in step 707 may be transmitted and deployed on the appropriate devices within the distributed architecture 100. For example, the firmware program configured to run on the implant 120 itself may be transmitted to the implant 120, and the therapy algorithm service software may be transmitted separately to the platform servers 110. In various embodiments, the firmware to be deployed on the implant 120 may be written in one or more programming languages, including C, C++, C#, and/or JAVA. The firmware may implement several different functions to be performed on the implant 120, including control the sampling of input data by the implant 120 (e.g., brain signals, accelerometer data, wireless signals, etc.). The firmware also may control the output registers of the microcontroller of the implant 120, which in turn may control implant stimulation and wireless radio output. Additionally, the firmware may implement the input-to-output logic within the implant 120, which may consist of Boolean logic, loops, signals processing, and any other functions expressible via the programming language used to create the firmware. In some cases, the complexity of the logic implemented within the firmware of the implant 120 may be limited by the choice of the microcontroller for the implant 120, and there may be a trade-off between performance of the firmware logic and functions, and the power efficiency of the implant 120. In some embodiments, the TDE execution device 610 and/or compiler 620 may design/modify the therapy algorithm service to include an initialization step for the firmware, as the implant 120 firmware may be loaded onto the device from the cloud.

III. Neuromodulation Therapy Simulator

Further aspects of the present disclosure relate to a neuromodulation therapy simulator configured to predict various neuromodulation therapy outcomes for therapy algorithms and environments designed via the TDE execution device 610 and/or other neuromodulation therapy systems. As illustrated by the examples and embodiments below, the successful simulation of neuromodulation therapies, including specific therapy algorithms executing on specific implants devices within specific subjects, may meaningfully accelerate the process of neuromodulation therapy development. For example, simulations may enable researchers and clinicians to understand various aspects of the performance of a therapy algorithm without needing to actually execute the algorithm via an implant device of a subject (or even in a non-implanted hardware test bench). As discussed above, therapy algorithms guide the evolution of therapy output stimulation parameters in response to certain inputs. Thus, a neuromodulation therapy simulator may access historical input data across a wide range of subjects in different situations and environments, to allow researchers and clinicians to predict what stimulation outputs might look like for new algorithms by running the new algorithms on historical data. As discussed below, various embodiments of therapy simulators also may perform predictions regarding implant power consumption and clinical outcomes of subjects.

In some embodiments, a neuromodulation therapy simulator may receive and analyze simulation input data (including a selected therapy algorithm and/or parameters), a subject identifier and/or subject profile/characteristics, an implant-device identifier, implant-device characteristics, and/or other additional devices within a distributed architecture 100. Based on the simulation input data, neuromodulation therapy simulator may execute neuromodulation therapy simulations based on data retrieved from neuromodulation therapy data stores and/or data repositories 170, and various outcomes from the neuromodulation therapy simulation may be reported to the user.

Referring again briefly to FIG. 6, as discussed above a neuromodulation therapy simulator 614 may be implemented within a TDE execution device 610. For example, the therapy simulator 614 may be implemented as software subcomponent of the TDE execution device 610, and may be activated via the user interface 615 to perform simulations on the therapy algorithms designed by the user via the TDE execution device 610. However, in other embodiments, a neuromodulation therapy simulator 614 need not be implemented within a TDE execution device 610, but may be designed and built as a standalone software system within the distributed architecture 100. Additionally, as shown in this example, the neuromodulation therapy simulator 614 may receive simulation input data from a user (e.g., directly or via the TDE execution device 610), and may execute the requested simulations based on retrieved previous instances of neuromodulation therapy data from therapy data stores within the platform servers 110 (e.g., cloud-based), and/or subject data repositories 170 (e.g., cloud-based).

Figure 9:
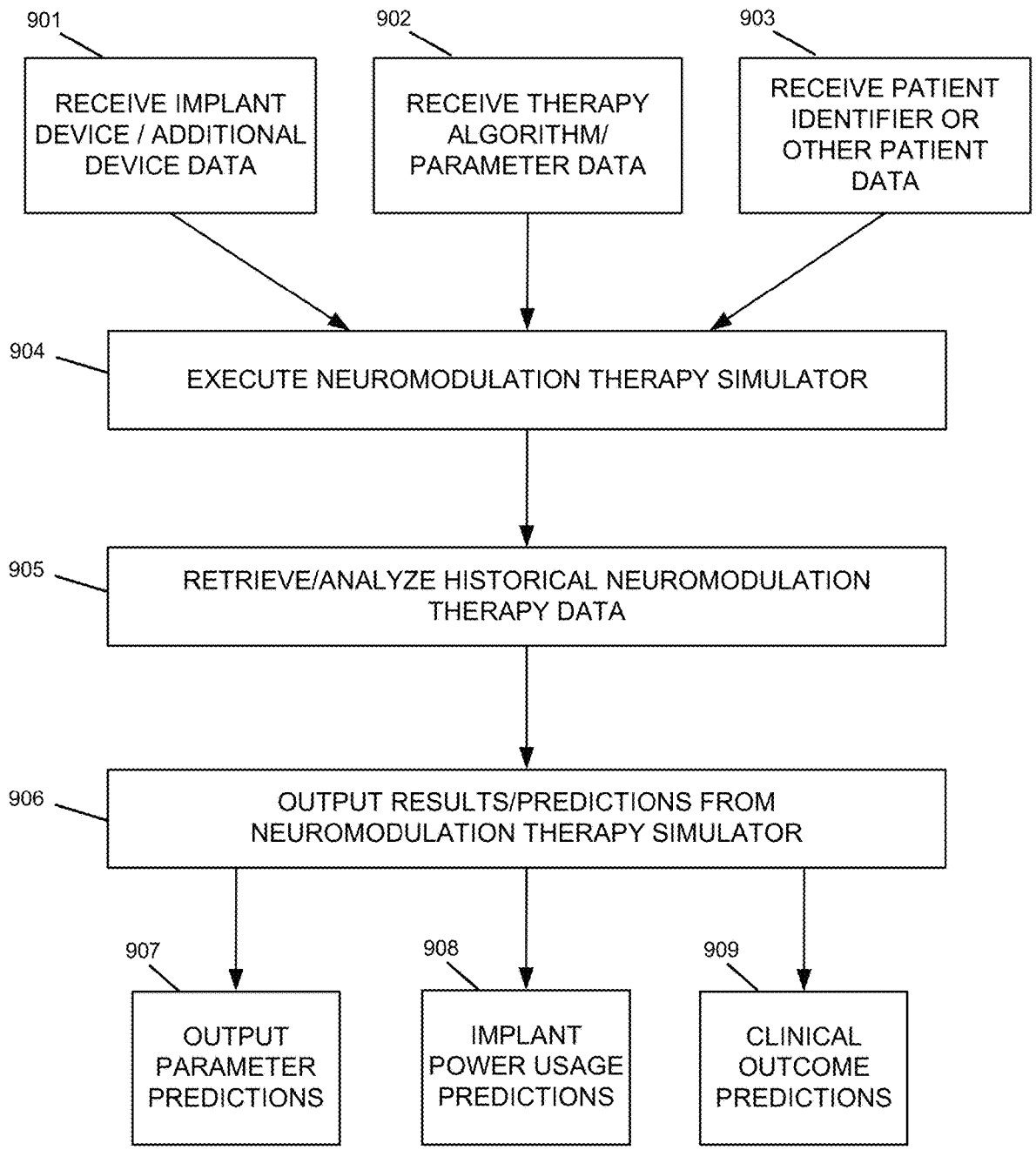
FIG. 9 is a flowchart of an example a process for executing a neuromodulation therapy simulator to predict outcomes of neuromodulation according to aspects of the present disclosure.

Referring now to FIG. 9, a flowchart is shown illustrating a process for executing a neuromodulation therapy simulator 614 to predict one or more outcomes of neuromodulation therapy based on a set of simulator inputs and analysis of the historic neuromodulation therapy data. In some embodiments, the steps in this process may be performed by a neuromodulation therapy simulator 614, which may be integrated within a TDE execution device 610 or implemented separately as a standalone simulator application 614 within a distributed architecture 100.

In steps 901-903, the therapy simulator 614 may receive three inputs that may be used define the scope of the neuromodulation therapy simulation to be performed. These input data need not be received in any particular order, and in some cases therapy simulations may be performed based on only one or two of these three input types 901-903. In step 901, the therapy simulator 614 may receive data identifying a neuromodulation therapy implant device 120 and/or additional devices/sensors within a distributed architecture 100. The additional devices/sensors may include, for example, the subject's mobile device(s) 130 and/or any other subject monitoring device described in reference to FIGS. 2A-2B. In step 902, the therapy simulator 614 may receive data identifying a therapy algorithm and/or therapy parameters. The received inputs for therapy algorithm and therapy parameters may correspond to any compatible combination of algorithm and/or parameters described herein. In step 903, the therapy simulator 614 may receive data identifying a particular subject, or a set of subject characteristics that may be used instead of an actual subject.

Generally speaking, the three types of input data received in steps 901-903 may be used to perform a neuromodulation therapy simulation. Such a simulation may be performed to predict the outcomes of neuromodulation therapy performed (a) on the identified subject (step 903), (b) assuming the identified implant device 120 has been implanted in the subject and/or that the other identified devices are present in the same distributed architecture 100 (step 901), and (c) using the received therapy algorithm and/or parameters (step 902). However, as noted above, for certain types of desired simulations and/or certain desired outcome predictions, it might not be necessary to receive all three types of input data 901-903, but instead simulations may be run using only one or two of these input types.

Figure 10A:
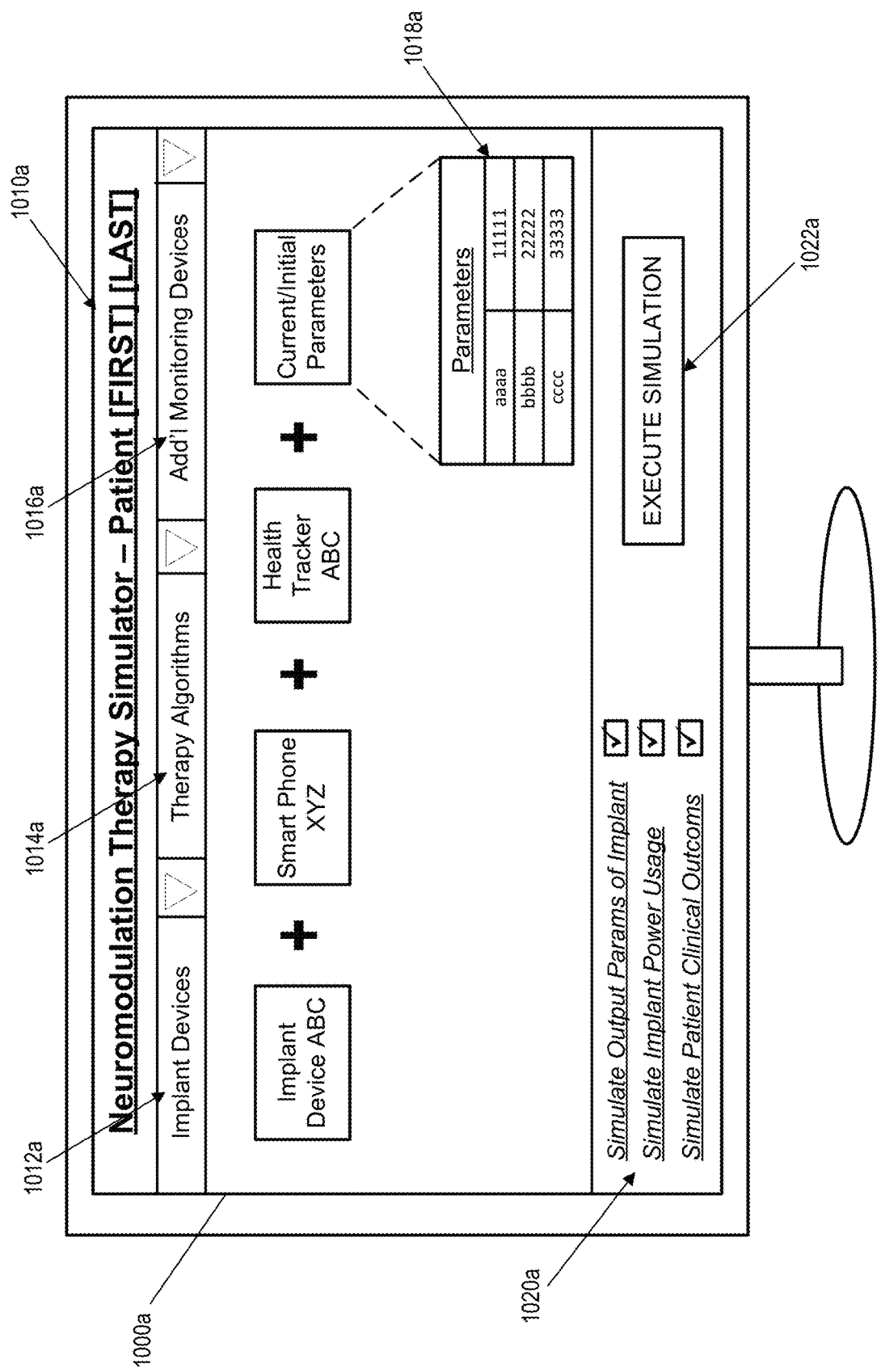
FIG. 10A illustrates an example graphical user interface for executing an underlying therapy simulator according to aspects of the present disclosure.

In step 904, the neuromodulation therapy simulator 614 may execute a simulation based the simulation input data received in steps 901-903. Referring briefly to FIG. 10A, an example graphical user interface 1000a is shown designed to execute an underlying therapy simulator 614. In this example, the interface includes the subject identification 1010a that represents a subject for whom the therapy simulation is the be run, which may be automatically defined as the current user of the interface 1000a, or may be a user-definable field. If an identification of a particular subject is not provided for the simulation, a set of subject characteristics may be defined instead, and the simulation may be run on a subject profile based on the characteristics. Examples of such characteristics may include the subject's condition, current and previous neuromodulation therapy data, current and previous biomarkers, current and previous symptoms, current and previous side-effects of therapy, subject age and demographic data, etc.

The interface 1000a also provides three dropdown GUI components 1012a, 1014a, and 1016a, to allow the user to select a particular implant device type (1012a), a particular therapy algorithm (1014a), and one or more additional subject monitoring devices (1016a) for the simulation. Finally, an editable parameter listing 1018a can be configured to allow the user to input therapy parameters to be used for the neuromodulation therapy simulation. After inputting the desired simulation data into the interface 1000a, the user may select the type(s) of simulation to be executed using checkboxes 1020a, and then may select the execute simulation button 1022a to initiate the neuromodulation therapy simulation by the therapy simulator 614.

In step 905, neuromodulation therapy simulation is performed by the therapy simulator 614. In some embodiments, the therapy simulation may be based on the retrieval and analysis of historical neuromodulation therapy data from one or more data repositories 170. For example, the therapy simulator 614 may query one or more data repositories 170 to received anonymized training data collected from the neuromodulation therapy data of previous subjects. The subject input identifier or profile data input into the simulator may be analyzed and classified based on either known health factors and/or initial biomarker feedback from the subject, and a cluster (or group) of subjects having similar physiological profiles may be identified. The therapy simulator 614 may then execute one or more models and/or data-driven algorithms using the group/cluster of subjects similar to the input subject data. The data underlying the models/algorithms may include the neuromodulation treatment algorithms and/or parameters for the subjects in the subject cluster, the implant devices (and other devices) used by the subjects in the subject cluster, and the various neuromodulation therapy outcomes that were experienced by the subjects resulting from their respective neuromodulation therapies. Using these general techniques various algorithms and/or trained models may be used to predict the subject outcomes for any other subject within the same group/cluster.

In some embodiments, the therapy simulator 614 may be configured to execute one or more machine learning algorithm(s) in step 905. In various supervised learning machine-learning algorithms, historical neuromodulation data may be used to train models to make predictions about the various outcomes from subject neuromodulation therapy. During the training process the model may be modified based on the accuracy of the output predictions, and the model training may continue until an optimal or desired level of prediction accuracy is reached. Various different supervised learning algorithms may be used to generate neuromodulation therapy models including, for example, a nearest neighbor algorithm, a naive Bayes algorithm, a decision tree algorithm, a linear regression algorithm, or a support vector machine algorithm. As discussed below, the therapy simulator 614 may output different types of results (e.g., stimulation predictions, implant power usage predictions, subject clinical outcome predictions, etc.). Accordingly, different types of machine-learning algorithms may be used, and/or different machine-learning models may be built, to output these different types of results. In other cases, a single model may be trained and used to output multiple different types of results, such as combinations of simulation data including implant stimulation, power usage, and clinical outcome predictions.

In step 906, the neuromodulation therapy simulation may complete, and the results output from the simulation may correspond to outcome predictions for the subject for the input neuromodulation therapy. As shown above with checkboxes 1020a, the therapy simulator 614 may be configured to perform a single simulation type or multiple different simulation types. In this example, different simulation types may correspond to different types of outcome predictions, which may include predictions regarding the stimulation output parameters of the implant device 120 (step 907), predictions regarding the power usage by the implant device 120 (step 908), and/or predictions regarding the clinical outcomes on the subject (step 909). In various embodiments, these different stimulation types may be performed by different therapy simulators 614 or may be performed together within a single simulation.

In step 907, the therapy simulator 614 may be configured to predict the stimulation output parameters of the implant 120. As discussed above, the stimulation output parameters refer to the parameter defining the electrical stimulation delivered by the implant 120 using the electrodes of the implant. The stimulation output parameters may include, for example, amplitude, frequency, pulse width, electrode configuration etc. A therapy algorithm may cause adjustments to these parameters, based on brain signals and other biomarkers detected by implant device 120. Thus, the predictions of the therapy simulator 614 in step 907 may correspond to predictions regarding what brain signals and biomarker data are likely to be detected by the implant device 120, and the subsequent adjustments that will be made to stimulation output parameters by the therapy algorithm. As noted above, these predictions of stimulation output parameters may be generated based on machine-learning algorithms and models based on historical data. Specifically, machine-learning generated models may be trained on a historical data from a combination of different subjects/subjects, different implant devices, different algorithms, etc. The training process for a model may include making predictions regarding how a therapy algorithm is likely to adjust the stimulation output parameters based on the type of algorithm, the subject-specific data, the specifications of the implant device 120, and the starting set of parameters. Those predictions then may be compared to historical data that indicates how an implant device 120 previously did adjust its stimulation output parameters using the same algorithm and under the same (or similar) conditions. The model may self-correct and learn based on the accuracy or inaccuracy of the predictions, until reaching an optimal or desired level of accuracy regarding the predictions of stimulation output parameters.

Researchers and/or clinicians may use predictions of stimulation output parameters in step 907 to see if, given historical input data, their algorithm is likely to cause the stimulation parameters to evolve in the desired way. For example, researchers may use the simulator output from step 907 to confirm that, given historical input data, a particular therapy algorithm is not likely to cause the stimulation parameters to oscillate unintentionally, or to rail out to a minimum or maximum and not recover. Much as with the design of feedback systems in integrated circuits, the design of algorithms for brain machine interface is complex enough that it often cannot be calculated algebraically and in fact must be simulated based on empirical models. In this case, the model comes from the historical record of subject data (e.g. brain signals).

In step 908, the therapy simulator 614 may be configured to predict the power consumption of the implant device 120, as the implant device 120 administers the neuromodulation therapy to the subject. For predicting power consumption of an implant device, the models for simulation may include factors such as the device battery model, stimulation power efficiency curves, and telemetry power efficiency curves. The power consumption predictions of the therapy simulator 614 in step 908 may be derived empirically (e.g., based on data sheets), or experimentally (e.g., based on benchtop or historical data). For example, machine-learning algorithms and models may be trained based on historical power consumption data for different implant devices, executing different neuromodulation therapy algorithms, and implanted within different subjects having different clinical characteristics. The simulations in step 908 may be used by researchers or clinicians, for example, to simulate new algorithms and quickly understand how much power those algorithms are likely to consume, and how often the subject may need to recharge or replace the battery on their implant device 120. Since battery recharge and replacement is a meaningful element of the subject experience, it would be technically advantageous to clinicians and researchers to better understand this metric. In fact, a key goal in some therapy algorithms is the reduction of power consumption and the maximization of implant battery life.

In step 909, the therapy simulator 614 may be configured to predict the clinical outcomes of a particular subject in response to the neuromodulation therapy delivered to the subject. The types of clinical outcomes that may be predicted in step 909 may include predicted changes to a subject's symptoms (e.g., tremors or motion symptoms), biomarkers, bulk clinical scores, medical condition, and/or overall subject state. The clinical outcome predictions of the therapy simulator 614 in step 909 may be determined based on historical data, using machine-learning algorithms and trained models. For example, machine learning models may be trained based on historical subject data corresponding to changes in clinical outcomes of subjects following different types and characteristics of neuromodulation therapies delivered to the subject, such as different therapy algorithms, parameters, types of implant devices 120, etc. The simulations in step 909 may be used by researchers or clinicians to predict likely clinical responses of different subjects to changes in neuromodulation therapy algorithms, implant devices 120, etc.

In some embodiments, clinical outcome predictions made by the therapy simulator 614 may be applicable at the individual subject level. For an individual subject, the more that subject uses a particular neuromodulation therapy, the more data may be available to build a subject-specific model describing how that neuromodulation therapy works for that subject. For example, if a deep brain stimulation therapy is also sensing brain signals of interest and sensing motion signals of interest (from the implant 120, a wearable, or the subject's mobile device 130) then over time the model will develop an understanding of the relationship between the subject's clinical state (e.g., as determined by the motion parameters) and the subject's stimulation parameters. Such subject-specific models may be used as the basis for determining whether an updated neuromodulation therapy algorithm is likely to result in a clinical improvement for the subject. Using such techniques, researchers or clinicians may be able to rapidly iterate through many different configurations of neuromodulation therapies (e.g., algorithms, parameters, implant types, etc.) using the software of the therapy simulator 614, in a way that would be impractical to do in real time for the subject.

Additionally, clinical outcome predictions made by the therapy simulator 614 may be applicable for predicting clinical outcomes from neuromodulation therapy within general larger populations. When greater amounts of historical data for clinical outcomes of subjects is available, trained models may establish links between stimulation of particular neural circuits and statistical likelihoods of measurable outcomes based on those stimulations. For example, the algorithm or model based on historical data may reveal that, given a certain measured brain state/signal, providing stimulation in a certain way may have the highest likelihood of achieving a desired clinical outcome (e.g., reduced tremors, mood improvement, etc.). As with the above examples, the models may be built from data from multiple subjects, and become more statistically accurate and powerful when more historical subject data is included.

Figure 10B:
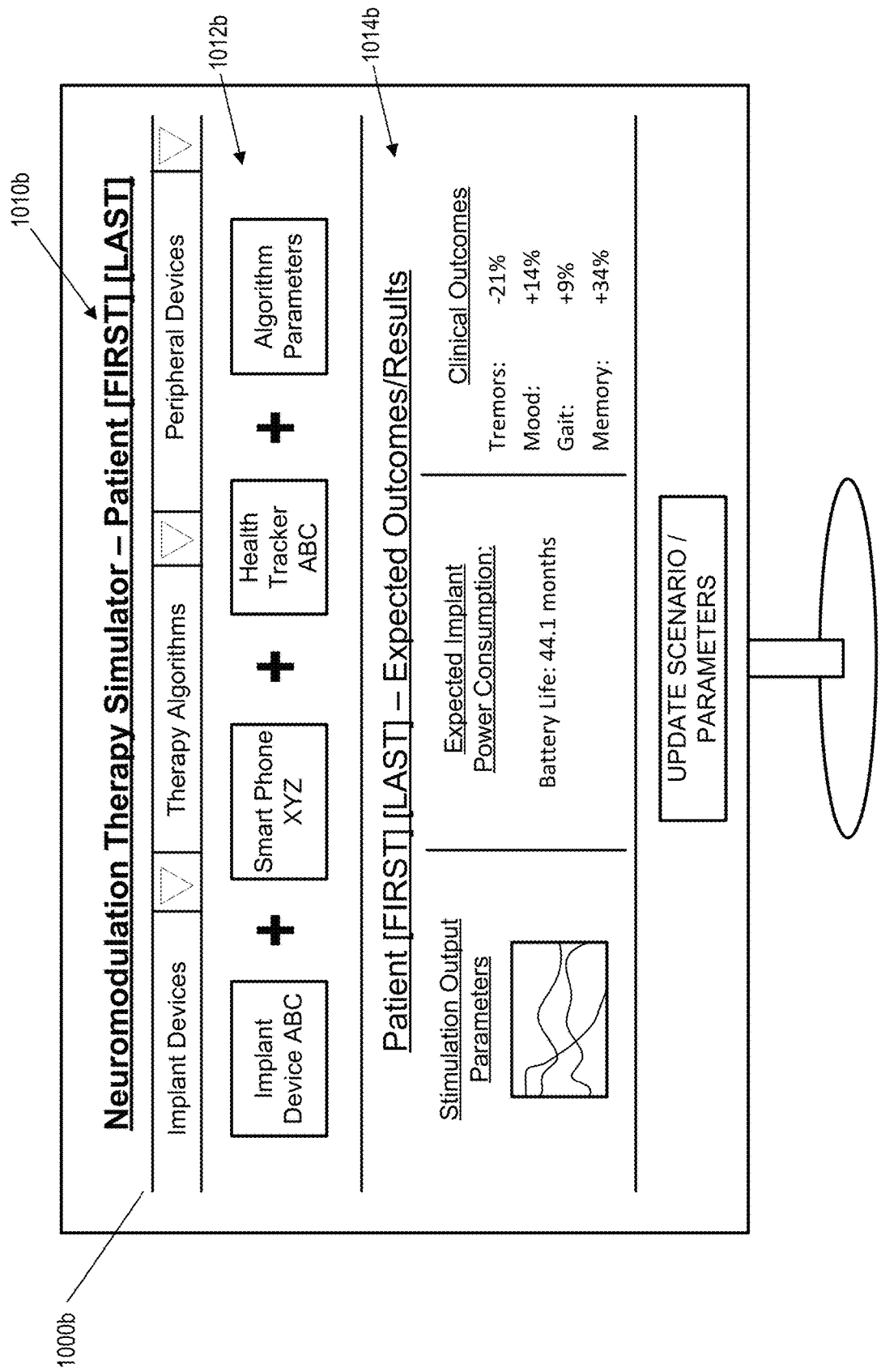
FIG. 10B illustrates an example graphical user interface displaying the output from the execution of a neuromodulation therapy simulator according to aspects of the present disclosure.

Referring briefly to FIG. 10B, an example interface 1000*b* is shown displaying the output from the execution of a neuromodulation therapy simulator 614. In this example, the subject 1010*b* and other simulator inputs 1012*b* are shown, along with the simulator output 1014*b* corresponding to predictions of the neuromodulation therapy outcomes for performing the neuromodulation therapy identified in the simulation inputs 1012*b*, on the particular subject 1010*b*. In this example, the predictions of the neuromodulation therapy outcomes in 1014*b* include projections for stimulation output parameters of the implant device 120, the expected implant power consumption rate, and the expected clinical outcomes for the subject.

IV. Security and Identity Verification for Neuromodulation Therapy Implant Device Programming Additional aspects described herein relate to securing access to neuromodulation therapy implant devices, including techniques for enforcing secure user/device identity verification prior to granting access to an implant device from a mobile device. When providing remote access to a subject's implant device 120, device identity verification and security can be highly important, especially where the remote access includes capabilities for controlling or modifying the subject's therapy parameters or other critic al data stored on the implant device 120. For connections made between various mobile devices and cloud-based platform servers 110, cloud services may be used to authenticate the mobile devices, and security/encryption can be managed with the cloud using widely available technology (e.g., SSL/TLS certificates). However, connections between a mobile device 130 and a subject's implant device 120 present significant technical challenges to assure that the mobile device 130 requesting access to the implant 120 may be trusted.

Conventional techniques for secure wireless pairing may rely on physical or visual access to both devices (e.g., manually entering a code on the device, pushing a button to acknowledge pairing, etc.). However, with regard to neuromodulation therapy implant devices 120 that have been implanted in the subject's body, physical or visual access to the implant devices 120 might not be possible. Existing solutions, such as using a proprietary format for the implant device radios, and/or supporting connections only at close-range, still leave implant devices 120 vulnerable to bad actors who may readily discover the proprietary radio format and/or may create high-power radios capable of spoofing a programmer/charger device in order to gain unauthorized access to a subject's implant device.

Figure 11:
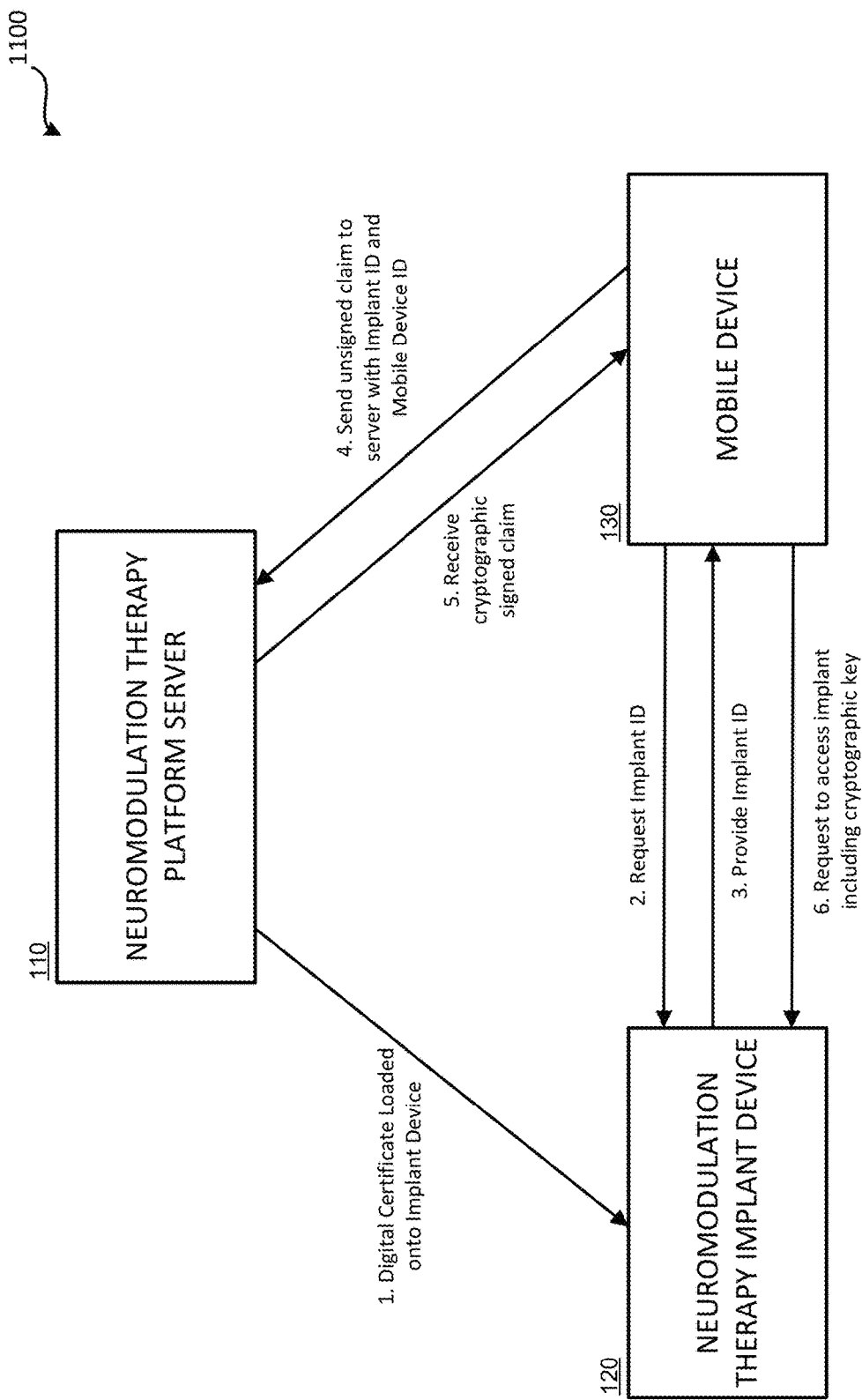
FIG. 11 illustrates an example of a neuromodulation therapy distributed computing environment according to aspects of the present disclosure.

Referring now to FIG. 11, a neuromodulation therapy distributed computing environment 1100 is shown, including sequential arrows 1-6 illustrating a technique for requesting/receive secure access grants from mobile devices 130 to a subject's neuromodulation therapy implant device 120. The distributed computing architecture 1100 may share components and functionalities with distributed computing environment 100.

Steps 1-6 in FIG. 11 illustrate a technique for providing secure access to a subject's implant device 120. These steps are described in more detail, and specifically from the perspective of the mobile device 130, below in FIG. 12. In Step 1, the platform server 110 may generate and provide an asymmetric encryption-key pair (or digital certificate) to be loaded onto the implant device 120. For example, the platform server (or other authorized actor) may generate a digital key pair with a known asymmetric encryption algorithm (e.g., RSA). The private key may be kept secret and stored securely on the platform server 110 (and in some embodiments, exclusively on the platform server 110). The public non-secret key, which may be in the form of a digital certificate, but is not necessarily a digital certificate, may be loaded into the implant device 120 during manufacturing/prior to use. The two keys may have a unique cryptographic relationship such that the private key can be used to generate a unique signature/digest of any data (e.g., request, claim), while the public key/certificate may have the sole ability to verify the authenticity of that signature. The public key cannot be used to generate signatures, so it can be shared publicly/insecurely or compromised by malicious users, without any consequence to the algorithm. In some examples, this process may occur during the manufacturing process for the implant device 120. It is further noted that the digital certificate provided in Step 1 need not be implant-specific, and also need not be a secret/private key. Additionally, although the platform server 110 may generate and provide the digital certificate in this example, in other cases the digital certificate may be generated and provided to the implant by a third-party system or other entity, before or after implantation of the implant device 120 into the subject. In Steps 2-3, the mobile device 130 may request and receive a unique implant identifier (or implant ID) from the implant device 120. At this time, the mobile device 130 may be unknown and untrusted to the implant device 120, but the implant ID is neither private nor secure. In Step 4-5, the mobile device 130 may send a "claim" and receive in return a cryptographically signed claim from the platform server 110, and in Step 6 the mobile device may use the signed claim to access to the implant device 120.

These steps, which are described in more detail below in reference to FIG. 12, may provide technical advantages that make large-scale deployment of implant devices 120 feasible for several reasons, in contrast to conventional techniques. For example, the digital certificates loaded onto the implant devices in Step 1 need not be secret keys, and also do not need to be unique to a particular implant. Additionally, this technique does not require physical access to the implant device 120 (which is likely to be implanted within the subject) in order to cryptographically pair the implant device 120 with the subject's mobile device 130. Additionally, this technique allows the subject to change mobile devices 130 and/or use multiple different mobile devices 130 to access the implant device 120. Finally, this technique provides additional security over conventional systems that rely on time windows and/or proprietary radio formats to provide security.

Figure 12:
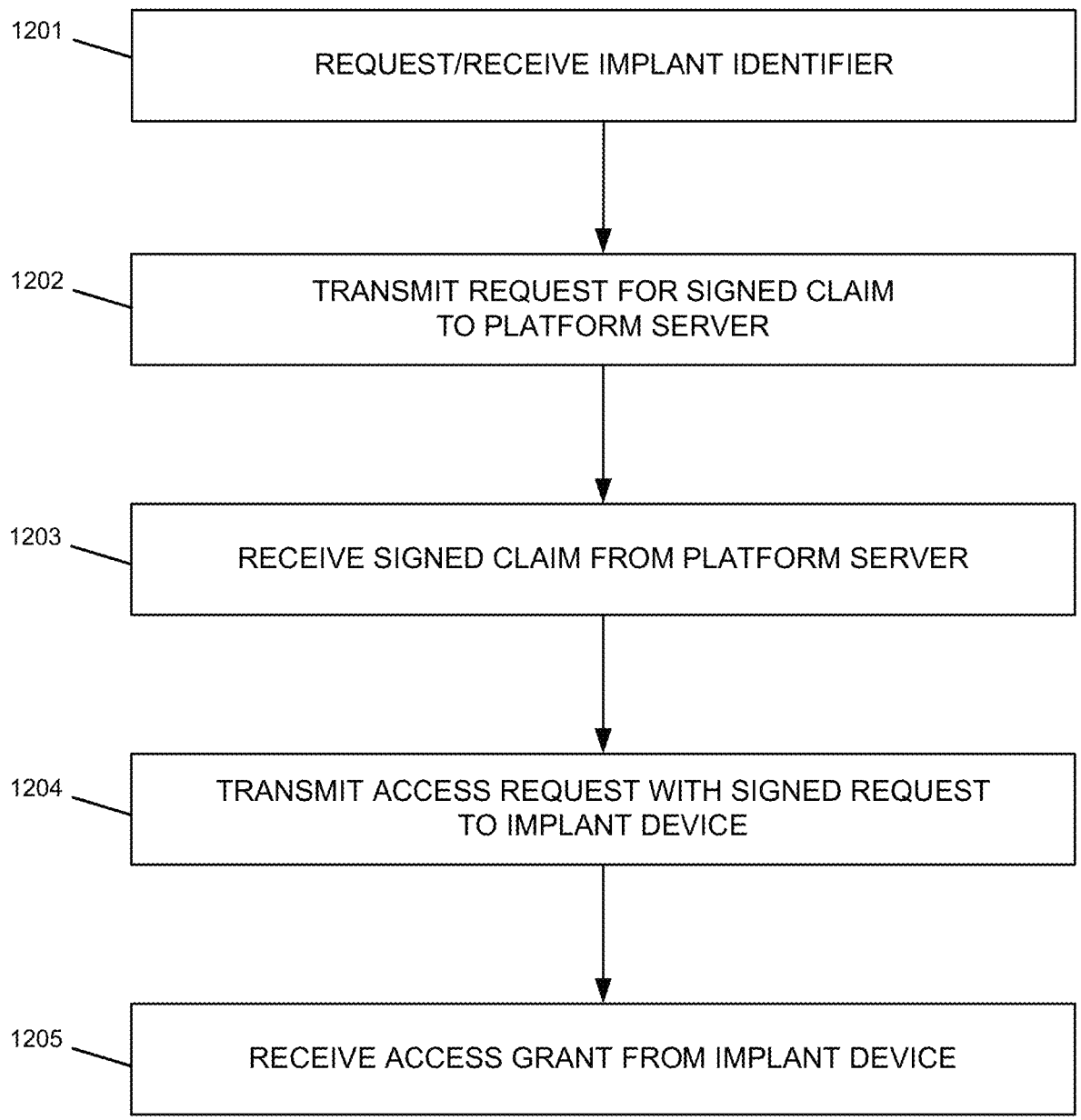
FIG. 12 is a flowchart of an example process for verifying and granting access to implant devices according to aspects of the present disclosure.

Referring now to FIG. 12, a flow chart is shown illustrating a related process, from the perspective of the mobile device 130, of verifying and granting the mobile device 130 access to the implant device 120. As discussed below, the steps in this process may be performed by a mobile device 130 to obtain access to an associated implant device 120. It should be understood that the mobile device 130 in this example may be initially entirely unknown and untrusted to the implant device 120. However, as discussed below, the platform server 110 may know in advance the intended users of a particular implant 120 (e.g., the subject, one or more clinicians, one or more researches, etc.), and may maintain a secure list of all pre-authorized users. This allows the techniques of FIGS. 11-12 to use a general certificate/signature pair structure, where a non-private digital certificate may be loaded onto each implant device 120, while each corresponding private signing key is stored outside the implant within the secure platform servers 110.

In step 1201, the mobile device 130 may request and receive an implant ID for the implant device 120 that it seeks to access. In some embodiments, the mobile device 130 may request/receive the implant ID from the implant device 120 itself. Alternatively, the platform server 110 or other system may provide the appropriate implant ID to the mobile device 130.

In step 1202, the mobile device 130 may transmit a request to the platform server 130 for a cryptographically signed claim for the implant device 120. In some embodiments, the request to the platform server 110 in step 1202 (which may be referred to as a "claim"), may include a user identifier of the user of the mobile device 130, and/or the implant ID for the implant device 120 that the mobile device is attempting to access. The request in step 1202 may be sent via a secure network connection with the platform server 110.

When the platform server 110 receives the request in step 1202, it may initially determine whether user information associated with the mobile device 130 is known, authenticated, and/or is authorized to access the particular implant device 120 that it is attempting to access. If so, the platform server may use the appropriate private key to generate a cryptographic signature and continue to subsequent steps.

In step 1203, the platform server 110 may transmit the cryptographically signed claim back to the mobile device 130. The signed claim received from the platform server 110 may include the private-key generated digital signature. Additionally, in some embodiments, the signed claim received in step 1203 also may include the level of permissions assigned to the user of the mobile device 130 (e.g., read access, read/write access, etc.), and/or an expiration date for the signed claim. The level of permissions may be used to enforce an authorized level of access to the implant device 120 by the mobile device 130, and the expiration date may prevent authentic signed claims from being stolen and re-used by bad actors to gain access to the implant device 120 at a later time.

In step 1204, the mobile device 130 may transmit the signed claim received from the platform server 110 to the implant device 120 to request access. As noted above, signed claim transmitted by the mobile device 130 to the implant 120 may include a user or device identifier associated with the mobile device 130, an indication of an authorized level of access for the user/device, and expiration date for the request. The implant device 120 may use its own digital certificate to cryptographically verify that the signed claim received from the mobile was generated with the corresponding private key to its own digital certificate. The implant device 120 may also verify the expiration date using its system clock, to confirm the validity of the signed claim.

In step 1205, the implant device 120 may respond to the mobile device 130, granting the requested level of access to the implant device 120, thereby allowing the mobile device 130 to receive transmissions of subject data (e.g., biomarkers) from the implant device 120, transmit updated therapy parameters to the implant device 120, and so on.

In some embodiments, physical "tokens" also may be used to put the implant device 120 into a "pairing mode" for pairing with the mobile device 130. For example a physical token may be used that transmits close range wireless signals to the implant 120, which may put the implant 120 into pairing mode, or may be used to acknowledge the desire to pair a new device with the implant 120. In various examples, a token may be a magnet that flips a reed switch in the implant device 120, or an RFID emitter that hits a backscatter coil in the implant 120. The use of tokens to put the implant device 120 into pairing mode may be advantageous, for example, where the primary radio connection is of a longer range (e.g., Bluetooth). Additionally, using a token to put the implant device 120 into pairing mode also may help prevent power-draining DDOS attacks.

V. Neuromodulation Therapy Data Subject Consent Matrix

Further aspects described herein relate to storage and maintenance of subject consent data within a neuromodulation therapy system. As discussed in the various aspects and embodiments described herein, the neuromodulation therapy platform (e.g., a cloud-based platform) 110 may provide and support various functionality for subjects, clinicians, researchers, therapy algorithm designers, and users of various other roles. Further, in a neuromodulation therapy system, individual subjects may be a primary source for a large amount of the data within the system, including the subject's neuromodulation therapy data (e.g., therapy algorithms and therapy parameters), and the subject's monitoring data (e.g., brain signals, biomarkers, monitoring of symptoms and side-effects, etc.). Accordingly, it may be advantageous to store this data within the neuromodulation therapy system using a subject-centric data model, such that the data on the platform may be organized on a subject-by-subject basis.

In order for subjects, clinicians, researchers, and other types of users to make use of the therapy platform, it may be important to know the data state and the access permissions of all underlying data at all times. Data state information may include, for example, the origin of the data, history of access of the data, and/or what the data is consented to be used for. For instance, certain data may have been consented for broad R&D usage, while other data may have been consented to narrowly for use by a single hospital. Furthermore, it may be advantageous for the therapy platform 110 to control data access across customers and institutions.

Accordingly, in some embodiments, a specialized data structure referred to herein as a subject consent matrix may be constructed for each subject data set. Using the subject consent matrix structures, each data set may be broken down into constituent and potentially overlapping parts, which individually may be granted consent. For example, a single subject data may include protected health information (PHI) of the subject, anonymized data, implant data, application data, etc., and for each constituent part there may be a record of what that data is consented to be used for, and by whom. These consent records also may evolve over time as people access and modify the original data set.

Figure 13:
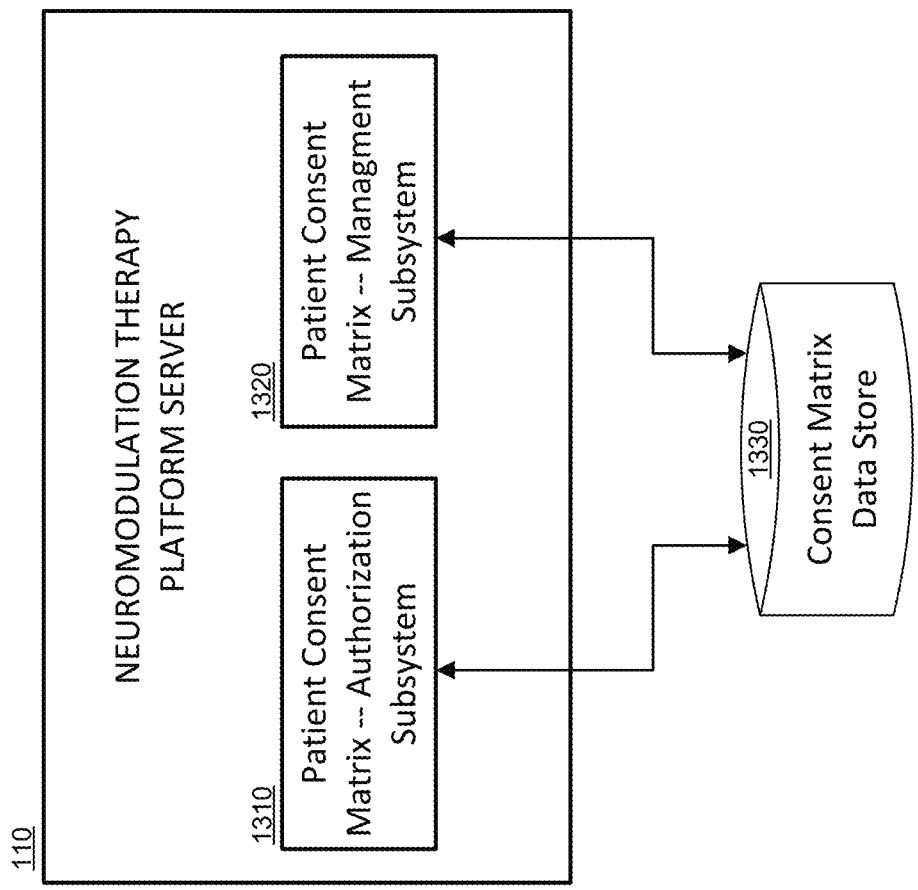
FIG. 13 illustrates a neuromodulation therapy computing environment according to aspects of the present disclosure.

Referring now to FIG. 13, a neuromodulation therapy computing environment is shown, including a data store and a system architecture configured to support a subject consent matrix, by tracking and storing consent data records associated with each data set and each modification made to each data set within the neuromodulation therapy system. In this example, the data defining the subject consent matrix may be stored in a data store 330, but the subject consent matrix may be enforced by an authorization subsystem 1310 and management subsystem operating within the platform servers 110.

In this example, the authorization subsystem 1310 may serves as an authority on the subject consent matrix, including storing a set of programmatic rules that represent each individual consent agreement. For any permutation of principal (e.g., subject, researcher, actor requesting access), action (e.g., read, modify, etc.), and/or dataset (e.g., uniquely identified, or by secondary context such the subject-owner of the data, etc.), the authorization subsystem 1310 may search for applicable rules. Those rules then may be evaluated in priority order to approve or deny access to particular subject data. In some embodiments, any internal or external component which may act upon a given principal's request to retrieve or modify a dataset may be required to first clear the request with the authorization subsystem 1310. The rule set also may serve as a method of validating new consent agreements by ensuring that new rules cannot be added which contradict or violate those of an existing, still-binding agreement.

Additionally, in this example, a management subsystem 1320 may serve as an immutable ledger for all datasets and their transformations. Every initial data ingestion, may be recorded in the ledger, assigning both a unique identifier to the dataset, as well as any additional context (e.g., subject owner, time, etc.). When any internal or external component makes a modification to a dataset, splits, or combines multiple datasets, the transaction may be recorded in the ledger, such that the new version of the data set produced by the transformation may be tracked independently, and also may have its lineage traced back to the original dataset(s) from which it was produced. With this trace, authorization requests can then accurately determine which combined set of consent matrix rules are applicable to each version of each dataset, and may enforce access accordingly based on the applicable consent matrix rules.

Figure 14A:
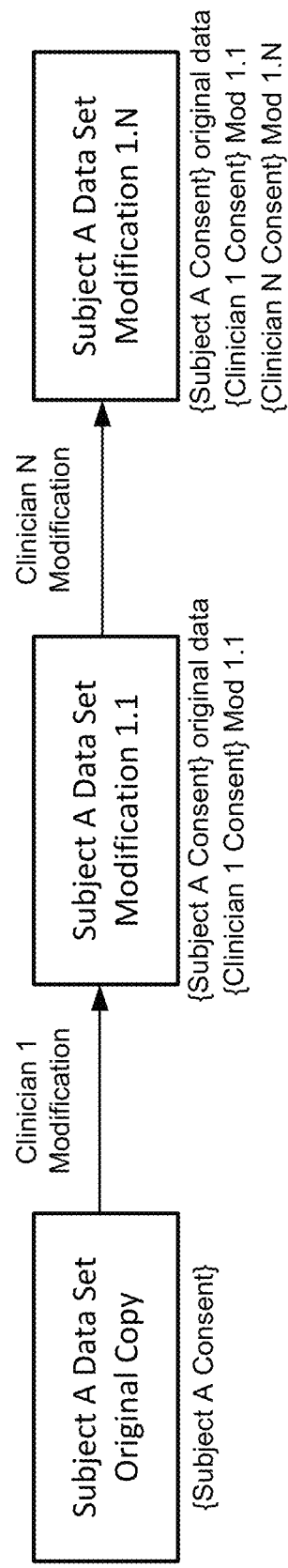
FIG. 14A is a block diagram illustrating a modification to data set and corresponding consent data according to aspects of the present disclosure.
Figure 14B:
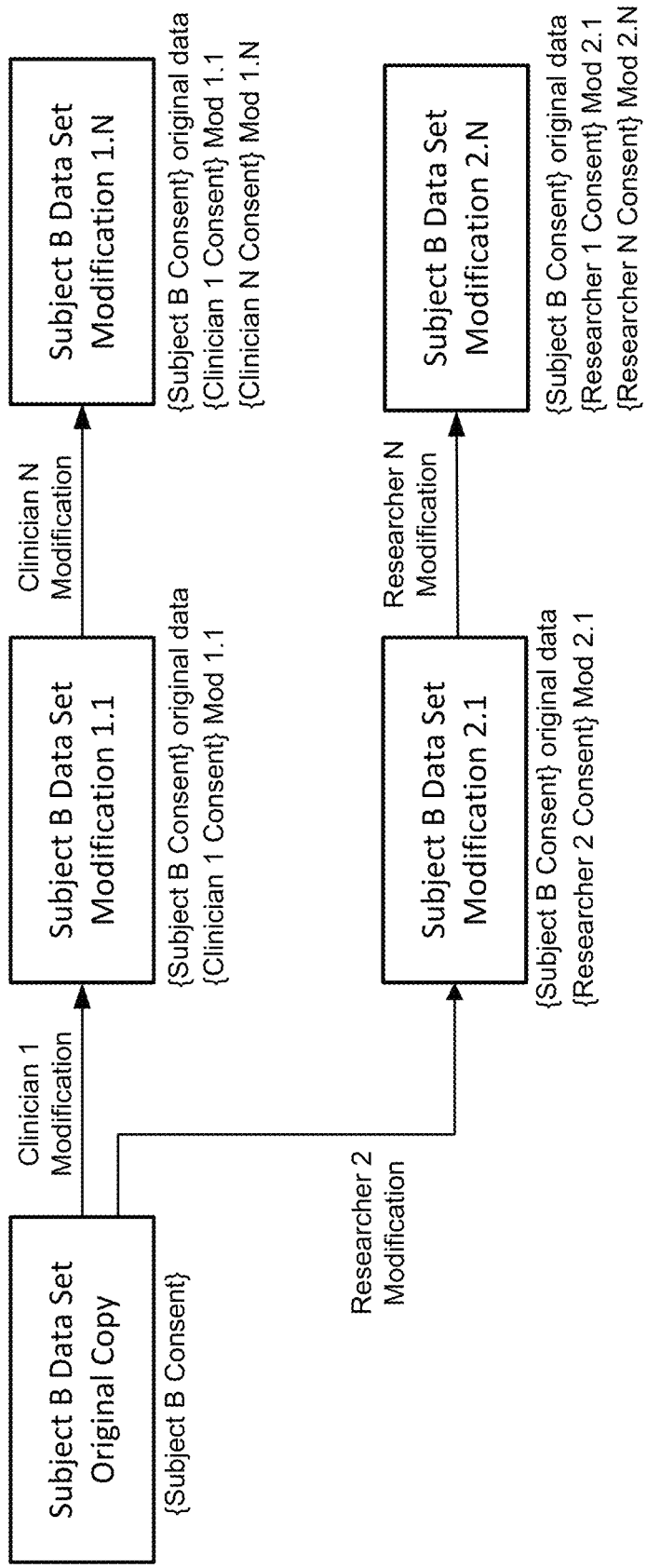
FIG. 14B is a block diagram illustrating a series of modification to data set and corresponding consent data according to aspects of the present disclosure.
Figure 14C:
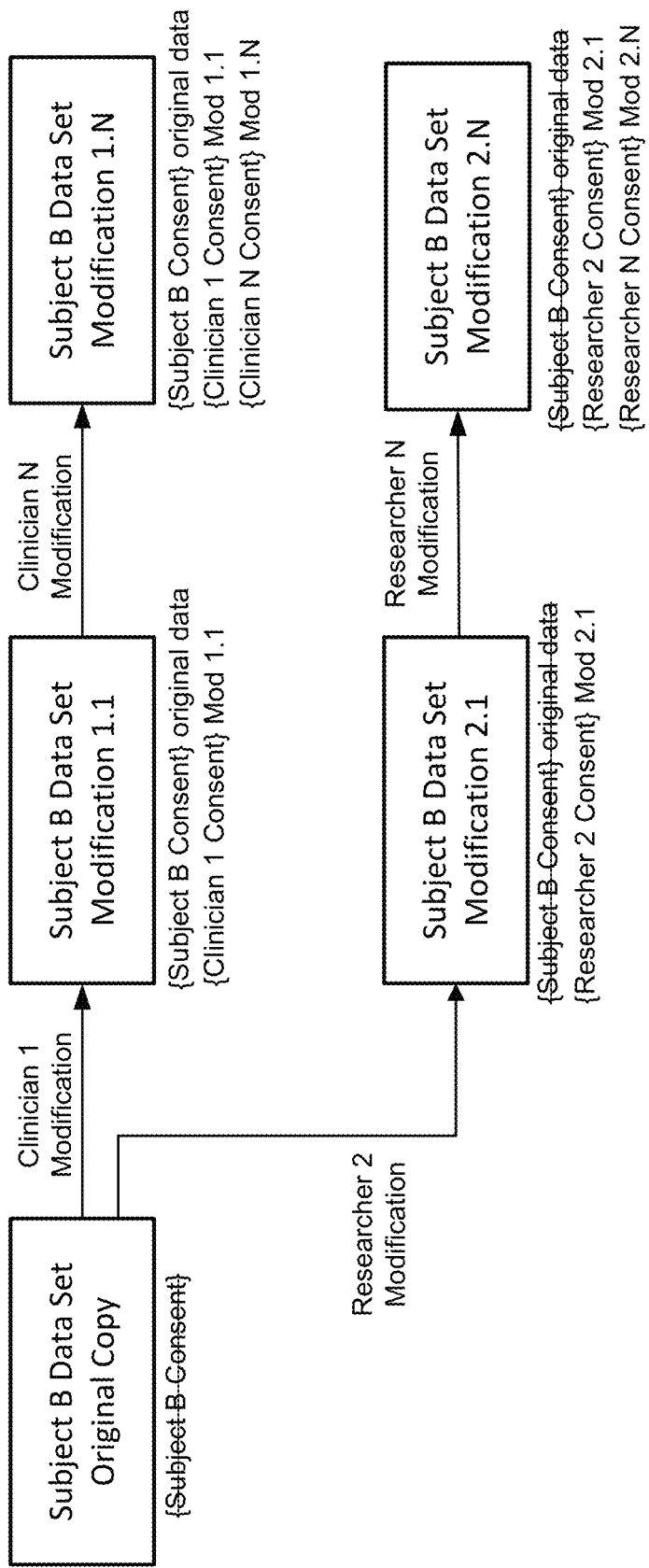
FIG. 14C is a block diagram illustrating modification to consent data being propagated through a series of modification to a data set according to aspects of the present disclosure.

Referring now to FIGS. 14A-14C, an example is shown illustrating data sets and corresponding consent data that may be stored by a subject consent matrix (or subject consent matrix), such as consent matrix 1310-1330 discussed above. Each box in FIGS. 14A-14C represents a unique data set of subject data (e.g., subject data), such as a subject's neuromodulation therapy data, a subject's monitoring data, etc. The left-to-right arrows in FIGS. 14A-14C indicate that a subject's original data set (on the far left side of each figure) may be modified over time by various parties (e.g., the subject, various clinicians and researchers, etc.), and each modification to a data set is shown as a new box (moving progressively to the right). If the same data set is modified by two different parties, then the left-to-right progression may branch as shown in FIGS. 4B and 4C.

Additionally, for each data set and for each modification of each data set, the consent matrix may store corresponding consent data from one or more parties associated with the data set. In FIGS. 14A-14C, the consent data is represented by the lines within braces below the box representing each data set. Each consent data associated with a data set represents consent given by a party (e.g., the subject, a clinician, a researcher, etc.) allowing one or more other parties with access to the data set. Each consent data may include data identifying the parties to which access has been granted, the type or level of access (e.g., read-only, read-write, anonymized or user-identified data, etc.), the permissible purpose of the access (e.g., for research purposes, clinical purposes, etc.), and for how long the access is granted. Further, each time a data set is modified, new consent data from the modifying party may be added to the data set. For instance, as shown in FIG. 14A, the original copy of the Subject A data set includes consent data from only Subject A. However, after the Subject A data set is modified by Clinician 1, the modified set data includes consent data both from Subject A and Clinician 1. After the modified Subject A data set is modified again by Clinician N, the twice-modified set data includes consent data from Subject A, Clinician 1, and Clinician N. Thus, each owner, author, or creator of the original data or any subsequent modification of the data may retain privileges over their own modified data set and any subsequent modifications to that data set.

When a data set has associated consent data from multiple different parties, it may be required that each different set of consent data must be satisfied before allowing access to the data set. For example, referring again to FIG. 14A, any request to access "Modification 1.1" of the Subject A data set must satisfy the original consent data defined by subject A and the additional "Mod 1.1" consent data defined by Clinician 1. Any request to access "Modification 1.N" of the Subject A data set must satisfy the original consent data defined by subject A, the "Mod 1.1" consent data defined by Clinician 1, and the "Mod 1.N" consent data defined by Clinician N, and so on.

Referring now to FIG. 14B, an example is shown of series of modifications to a data set of Subject B, along with the corresponding consent data. In this example, the original copy of the Subject B data set was modified by Clinician 1, and independently modified by Researcher 1. Thus, the subject consent matrix in this example stores the separate Subject B data sets (i.e., Modification 1.1 and Modification 2.1), as well as separate data sets for each of the subsequent modifications to those data sets (i.e., Modification 1.N and Modification 2.N). For each box shown in FIG. 14B, representing a separate Subject B data set, the consent data for that particular data set is shown below the corresponding box. Each consent data is different, and is based on the chain of modifications between each data set and the original copy of the Subject B data set. Thus, the subject consent matrix in this example stores data sets corresponding to the original copy of the data set, each subsequent modified copy of the data set, data indicating the relationships between the different modified copies of the data set, and the consent data associated with each different modified copy of the data set.

Referring now to FIG. 14C, this example shows a modification to the consent data shown in FIG. 14B, and illustrates that the change in the consent may be appropriately propagated throughout the series of modifications to the data set. For instance, FIG. 14C illustrates a scenario in which Subject B's consent B for research and development (R&D) use of the data set has either expired or was expressly revoked by Subject B. However, Subject B's consent for clinician access to the data set remains in place. Accordingly, in FIG. 14D, the Subject B consent for the original copy of the data set has been revoked (for R&D use) and this revocation has propagated through to the "Modification 2.1" and "Modification 2.N" data sets for which content also has been revoked by Subject B.

The foregoing description of the examples, including illustrated examples, has been presented only for the purpose of illustration and description and is not intended to be exhaustive or to limit the subject matter to the precise forms disclosed. Numerous modifications, combinations, adaptations, uses, and installations thereof can be apparent to those skilled in the art without departing from the scope of this disclosure. The illustrative examples described above are given to introduce the reader to the general subject matter discussed here and are not intended to limit the scope of the disclosed concepts.

What is claimed is:

1. A method of simulating neuromodulation therapy, comprising:
  receiving a first dataset corresponding to a particular neuromodulation-therapy implant device;
  receiving a second dataset corresponding to a particular neuromodulation-therapy algorithm;
  receiving a third dataset corresponding to a subject-record for a particular subject;
  determining, based on an execution of a neuromodulation-therapy simulator, one or more predicted performance metrics that is based on the particular neuromodulation-therapy implant device, the particular neuromodulation-therapy algorithm, and the subject-record for the particular subject, wherein the one or more predicted performance metrics correspond to one or more predicted physiological responses of the subject when the particular neuromodulation-therapy algorithm is executed by the particular neuromodulation-therapy implant device to control an electrical output of the particular neuromodulation-therapy implant device;
  wherein the predicted performance metrics of the neuromodulation-therapy simulator are determined using:
    a machine-learning algorithm that was trained using a set of historical neuromodulation-therapy subject records, wherein each historical neuromodulation-therapy subject record of the set of historical neuromodulation-therapy subject records comprised an identification of a neuromodulation-therapy algorithm executed on a subject associated with the historical neuromodulation-therapy subject record; and
    subject outcome data characterizing an outcome following the execution of the neuromodulation-therapy algorithm; and
  outputting the one or more predicted performance metrics corresponding to the one or more predicted physiological responses of the subject.

2. The method of simulating neuromodulation therapy of claim 1, further comprising:
  determining one or more probability values associated with each of the predicted physiological responses determined for the subject.

3. The method of simulating neuromodulation therapy of claim 1, wherein determining the predicted performance metrics comprises:
  retrieving historical data corresponding to a plurality of previous neuromodulation-therapy subject records, and performing a regression analysis on the historical data.

4. The method of simulating neuromodulation therapy of claim 1, further comprising:
  training the machine-learning algorithm using the set of historical neuromodulation-therapy subject records.

5. The method of simulating neuromodulation therapy of claim 1, wherein the predicted performance metrics further comprise predicted power consumption by the particular neuromodulation-therapy implant device, wherein the predicted power consumption is based on the particular neuromodulation-therapy implant device, the particular neuromodulation-therapy algorithm, and the subject-record for the particular subject.

6. The method of claim 1, wherein the particular neuromodulation-therapy algorithm uses ensemble machine learning.

7. The method of claim 1, wherein the particular neuromodulation-therapy algorithm is based on Hidden Markov Model.

8. A system comprising:
  one or more data processors; and
  a non-transitory computer-readable storage medium storing instructions which, when executed by the one or more data processors, cause the one or more data processors to perform operations including:
    receiving a first dataset corresponding to a particular neuromodulation-therapy implant device;
    receiving a second dataset corresponding to a particular neuromodulation-therapy algorithm;
    receiving a third dataset corresponding to a subject-record for a particular subject;
    determining, based on an execution of a neuromodulation-therapy simulator, one or more predicted performance metrics that is based on the particular neuromodulation-therapy implant device, the particular neuromodulation-therapy algorithm, and the subject-record for the particular subject, wherein the one or more predicted performance metrics correspond to one or more predicted physiological responses of the subject when the particular neuromodulation-therapy algorithm is executed by the particular neuromodulation-therapy implant device to control an electrical output of the particular neuromodulation-therapy implant device, wherein the predicted performance metrics of the neuromodulation therapy simulation are determine using a machine-learning algorithm that was trained using a set of historical neuromodulation-therapy subject records, wherein each historical neuromodulation-therapy subject record of the set of historical neuromodulation-therapy subject records comprised an identification of a neuromodulation-therapy algorithm executed on a subject associated with the historical neuromodulation-therapy subject records and subject outcome data characterizing an outcome following the execution of the neuromodulation-therapy algorithm; and
    outputting the one or more predicted performance metrics corresponding to the one or more predicted physiological responses of the subject.

9. The system of claim 8, wherein the operations further include:
  determining one or more probability values associated with each of the predicted physiological responses determined for the subject.

10. The system of claim 8, wherein determining the predicted performance metrics comprises:
  retrieving historical data corresponding to a plurality of previous neuromodulation-therapy subject records, and performing a regression analysis on the historical data.

11. The system of claim 8, wherein the operations further include:
  training the machine-learning algorithm using the set of historical neuromodulation-therapy subject records.

12. The system of claim 8, wherein the predicted performance metrics further comprise predicted power consumption by the particular neuromodulation-therapy implant device, wherein the predicted power consumption is based on the particular neuromodulation-therapy implant device, the particular neuromodulation-therapy algorithm, and the subject-record for the particular subject.

13. The system of claim 8, wherein the particular neuromodulation-therapy algorithm uses ensemble machine learning.

14. The system of claim 8, wherein the particular neuromodulation-therapy algorithm is based on Hidden Markov Model.

15. A non-transitory computer-readable storage medium storing instructions which, when executed by one or more data processors, cause the one or more data processors to perform operations including:
  receiving a first dataset corresponding to a particular neuromodulation-therapy implant device;
  receiving a second dataset corresponding to a particular neuromodulation-therapy algorithm;
  receiving a third dataset corresponding to a subject-record for a particular subject;
  determining, based on an execution of a neuromodulation-therapy simulator, one or more predicted performance metrics that is based on the particular neuromodulation-therapy implant device, the particular neuromodulation-therapy algorithm, and the subject-record for the particular subject, wherein the one or more predicted performance metrics correspond to one or more predicted physiological responses of the subject when the particular neuromodulation-therapy algorithm is executed by the particular neuromodulation-therapy implant device to control an electrical output of the particular neuromodulation-therapy implant device, wherein the predicted performance metrics of the neuromodulation therapy simulation are determine using a machine-learning algorithm that was trained using a set of historical neuromodulation-therapy subject records, wherein each historical neuromodulation-therapy subject record of the set of historical neuromodulation-therapy subject records comprised an identification of a neuromodulation-therapy algorithm executed on a subject associated with the historical neuromodulation-therapy subject records and subject outcome data characterizing an outcome following the execution of the neuromodulation-therapy algorithm; and
  outputting the one or more predicted performance metrics corresponding to the one or more predicted physiological responses of the subject.

16. The non-transitory computer-readable storage medium of claim 15, wherein the operations further include:
  determining one or more probability values associated with each of the predicted physiological responses determined for the subject.

17. The non-transitory computer-readable storage medium of claim 15, wherein determining the predicted performance metrics comprises:
  retrieving historical data corresponding to a plurality of previous neuromodulation-therapy subject records, and
  performing a regression analysis on the historical data.

18. The non-transitory computer-readable storage medium of claim 15, wherein the operations further include:
  training the machine-learning algorithm using the set of historical neuromodulation-therapy subject records.

19. The non-transitory computer-readable storage medium of claim 15, wherein the predicted performance metrics further comprise predicted power consumption by the particular neuromodulation-therapy implant device, wherein the predicted power consumption is based on the particular neuromodulation-therapy implant device, the particular neuromodulation-therapy algorithm, and the subject-record for the particular subject.

20. The non-transitory computer-readable storage medium of claim 15, wherein the particular neuromodulation-therapy algorithm uses ensemble machine learning.

* * * * *